United States Patent
Oxford et al.

(10) Patent No.: US 7,429,607 B2
(45) Date of Patent: Sep. 30, 2008

(54) 5-HT$_{2B}$ RECEPTOR ANTAGONISTS

(75) Inventors: Alexander William Oxford, Hertfordshire (GB); Richard Anthony Borman, Cambridge (GB); Robert Alexander Coleman, Hertfordshire (GB); Kenneth Lyle Clark, Cambridge (GB); George Hynd, Essex (GB); Janet Ann Archer, Essex (GB); Amanda Aley, Essex (GB); Neil Victor Harris, Essex (GB)

(73) Assignee: Asterand UK Limited, Hertfordshire (GB)

( * ) Notice: Subject to any disclaimer, the term of this patent is extended or adjusted under 35 U.S.C. 154(b) by 523 days.

(21) Appl. No.: 10/364,672

(22) Filed: Feb. 12, 2003

(65) Prior Publication Data

US 2004/0010022 A1 Jan. 15, 2004

Related U.S. Application Data

(60) Provisional application No. 60/358,717, filed on Feb. 25, 2002.

(30) Foreign Application Priority Data

Feb. 13, 2002 (GB) ................................ 0203412.2

(51) Int. Cl.
*A61K 31/42* (2006.01)
*A61K 31/445* (2006.01)
*A61K 31/55* (2006.01)
*C07D 263/00* (2006.01)
*C07D 413/00* (2006.01)
*C07D 419/00* (2006.01)
*C07D 403/00* (2006.01)

(52) U.S. Cl. .................. 514/377; 548/233; 548/235; 546/209; 540/602; 540/603; 514/326; 514/217.09

(58) Field of Classification Search ................ 514/377, 514/326, 217.09; 548/233, 235; 540/602, 540/603; 546/209
See application file for complete search history.

(56) References Cited

U.S. PATENT DOCUMENTS

| 5,679,678 A | 10/1997 | Binder et al. ............ 514/226.5 |
| 5,952,331 A | 9/1999 | Berger et al. |
| 5,958,934 A | 9/1999 | Berger et al. |
| 6,177,452 B1 * | 1/2001 | Momose et al. ............ 514/377 |

FOREIGN PATENT DOCUMENTS

| WO | WO 95/24200 | 8/1995 |
| WO | WO 96/24351 | 9/1996 |
| WO | WO 97/44326 | 11/1997 |
| WO | WO 00/23444 | 4/2000 |
| WO | WO 01/08668 A2 | 2/2001 |
| WO | WO 01/14372 | 3/2001 |

OTHER PUBLICATIONS

Bansal, E., et al., *Ind. J. Chem.*, 39B, 357-362 (2000).
Berge, et al., 1977, *J. Pharm. Sci.*, 66, 1-19.
Cockerill, A.F., et al., *Synthesis*, 1976, 591-593.
Cooper, C., et al., *J. Med. Chem.*, 33, 1246-1252 (1990).
Crank, G. and Foulis, J., *J. Med, Chem.*, 14(11), 1075-1077 (1971).
Crank, G. and Kahn., H.R., *Aust. J. Chem.*, 38, 447-458 (1985).
Gompper, R., and Christmann, O., *Chem. Ber.* 92, 1944-1949 (1959).
Hoyer, et al., *Pharm. Rev.*, 46, 157-203 (1994).
Martin and Humphrey, *Neuropharm.*, 33, 261-273 (1994).
Launay, J.M., et al., *Nature Medicine*, 8(10), 1129-1135 (2002).
Nath, J., et al., *Ind. J. Chem.*, 20B, 606-607 (1981).
Pattanayak, B., et al., *J. Ind. Chem. Soc.*, 16B, 1030-1032 (1978).
Pattanayak, B., et al., *J. Ind. Chem. Soc.*, 55, 264-267 (1978).
Newton et al, Microwaves—A Short Path from the Cook's Kitchen to the Chemist's Laboratory, Global Outsourcing Review, vol. 5, No. 2, May 2003, pp. 1-5.
Bansal et al., "Synthesis and anti-inflammatory activity of 1-acetyl-5-substitute daryl-3-(β-aminonaphthyl)-2-pyrazolines and β-(substituted aminoethyl) amidonaphthalenes", Eur. J. Med. Chem. 36 (2001) 81-92.

(Continued)

Primary Examiner—Shengjun Wang
(74) Attorney, Agent, or Firm—Nixon & Vanderhye P.C.

(57) ABSTRACT

The present invention relates to compounds of formula I:

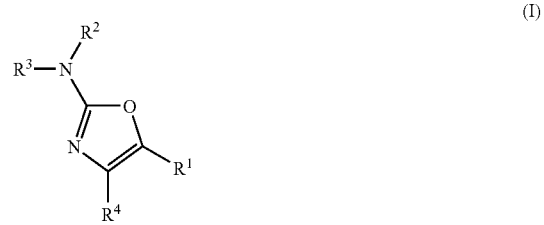

(I)

wherein one of $R^1$ and $R^4$ is selected from the group consisting of H, and optionally substituted $C_{1-6}$ alkyl, $C_{3-7}$ cycloalkyl, $C_{3-7}$ cycloalkyl-$C_{1-4}$ alkyl, and phenyl-$C_{1-4}$ alkyl; and the other of $R^1$ and $R^4$ is an optionally substituted $C_{9-14}$ aryl group; $R^2$ and $R^3$ are either:

(i) independently selected from H, R, R', $SO_2R$, $C(=O)R$, $(CH_2)_nNR^5R^6$, where n is from 1 to 4 and $R^5$ and $R^6$ are independently selected from H and R, where R is optionally substituted $C_{1-4}$ alkyl, and R' is optionally substituted phenyl-$C_{1-4}$ alkyl, or (ii) together with the nitrogen atom to which they are attached, form an optionally substituted $C_{5-7}$ heterocyclic group; and their use as pharmaceuticals, in particular for treating conditions alleviated by the antagonism of a 5-HT$_{2B}$ receptor.

16 Claims, No Drawings

OTHER PUBLICATIONS

Chemical Abstract 2000-100698 & Bansal et al., Oriental Journal of Chemistry, 15(3), 489-494.
Belstein, Registry No. 985793, XP-002239724, (Nov. 29, 1998).
Belstein, Registry No. 1213623, SP-002239725, (Nov. 29, 1988).
Chemical Abstracts, vol. 66, 1967, p. 8886.
Molina et al., Synthesis (1993) (1), 54-6 (Abstract).

* cited by examiner

5-HT$_{2B}$ RECEPTOR ANTAGONISTS

The present application claims benefit of U.S. Provisional Application No. 60/358,717, filed 25 Feb. 2002, the entire contents of which is incorporated herein by reference.

This invention relates to 5-HT$_{2B}$ receptor antagonists, pharmaceutical compositions comprising such compounds, and the use of such compounds and compositions to treat various diseases.

The entire contents of all references cited herein are incorporated herein by reference.

BACKGROUND TO THE INVENTION

Serotonin, also referred to as 5-hydroxytryptamine (5-HT), is a neurotransmitter with mixed and complex pharmacological characteristics. 5-HT acts via a number of discrete 5-HT receptors. Currently, fourteen subtypes of serotonin receptor are recognised and delineated into seven families, 5-HT$_1$ to 5-HT$_7$. Within the 5-HT$_2$ family, 5-HT$_{2A}$, 5-HT$_{2B}$ and 5-HT$_{2C}$ subtypes are known to exist. The nomenclature and classification of 5-HT receptors has been reviewed by Martin and Humphrey, *Neuropharm.*, 33, 261-273 (1994) and Hoyer, et al., *Pharm. Rev.*, 46, 157-203 (1994).

There is evidence to suggest a role for 5-HT$_{2B}$ receptors in a number of medical disorders, and therefore 5-HT$_{2B}$ receptor antagonists are likely to have a beneficial effect on patients suffering these disorders. They include, but are not limited to: disorders of the GI tract, and especially disorders involving altered motility, and particularly irritable bowel syndrome (WO 01/08668); disorders of gastric motility, dyspepsia, GERD, tachygastria; migraine/neurogenic pain (WO 97/44326); pain (U.S. Pat. No. 5,958,934); anxiety (WO 97/44326); depression (WO 97/44326); benign prostatic hyperplasia (U.S. Pat. No. 5,952,331); sleep disorder (WO 97/44326); panic disorder, obsessive compulsive disorder, alcoholism, hypertension, anorexia nervosa, and priapism (WO 97/44326); asthma and obstructive airway disease (U.S. Pat. No. 5,952,331); incontinence and bladder dysfunction (WO 96/24351); disorders of the uterus, such as dysmenorrhoea, pre-term labour, post-partum remodelling, endometriosis and fibrosis; pulmonary hypertension (Launay, J. M., et al., *Nature Medicine*, 8(10), 1129-1135 (2002)).

WO 97/44326 describes aryl pyrimidine derivatives and their use as selective 5-HT$_{2B}$ antagonists. However, although this application discloses a number of compounds, it is desirable to find further classes of compounds to act as 5-HT$_{2B}$ antagonists, which are preferably selective against 5-HT$_{2A}$ and 5-HT$_{2C}$ receptors.

SUMMARY OF THE INVENTION

A first aspect of the present invention provides a pharmaceutical composition comprising a compound of formula I:

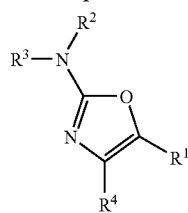

or a pharmaceutically acceptable salt thereof, together with a pharmaceutically acceptable carrier or diluent, wherein one of R$^1$ and R$^4$ is selected from the group consisting of H, and optionally substituted C$_{1-6}$ alkyl, C$_{3-7}$ cycloalkyl, C$_{3-7}$ cycloalkyl-C$_{1-4}$ alkyl, and phenyl-C$_{1-4}$ alkyl; and the other of R$^1$ and R$^4$ is an optionally substituted C$_{9-14}$ aryl group;

R$^2$ and R$^3$ are either:
  (i) independently selected from H, R, R', SO$_2$R, C(=O)R, (CH$_2$)$_n$NR$^5$R$^6$, where n is from 1 to 4 and R$^5$ and R$^6$ are independently selected from H and R, where R is optionally substituted C$_{1-4}$ alkyl, and R' is optionally substituted phenyl-C$_{1-4}$ alkyl, or
  (ii) together with the nitrogen atom to which they are attached, form an optionally substituted C$_{5-7}$ heterocyclic group;

with the proviso that when R$^1$, R$^2$ and R$^3$ are H, then R$^4$ is not:

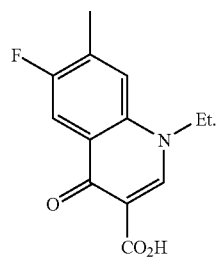

A second aspect of the present invention provides a compound of formula I:

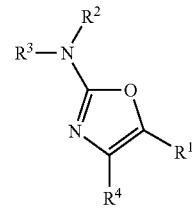

or a salt, solvate and chemically protected form thereof, wherein
one of R$^1$ and R$^4$ is selected from the group consisting of H, and optionally substituted C$_{1-6}$ alkyl, C$_{3-7}$ cycloalkyl, C$_{3-7}$ cycloalkyl-C$_{1-4}$ alkyl, and phenyl-C$_{1-4}$ alkyl;
and the other of R$^1$ and R$^4$ is an optionally substituted C$_{9-14}$ aryl group;
R$^2$ and R$^3$ are either:
  (i) independently selected from H, R, R', SO$_2$R, C(=O)R, (CH$_2$)$_n$NR$^5$R$^6$, where n is from 1 to 4 and R$^5$ and R$^6$ are independently selected from H and R, where R is optionally substituted C$_{1-4}$ alkyl, and R' is optionally substituted phenyl-C$_{1-4}$ alkyl, or
  (ii) together with the nitrogen atom to which they are attached, form an optionally substituted C$_{5-7}$ heterocyclic group;

with the provisos that when R$^4$ is napth-1-yl or napth-2-yl, R$^1$ and R$^2$ are hydrogen, R$^3$ is not hydrogen or:

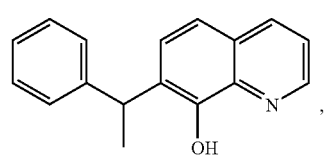

and that when $R^1$, $R^2$ and $R^3$ are hydrogen, $R^4$ is not:

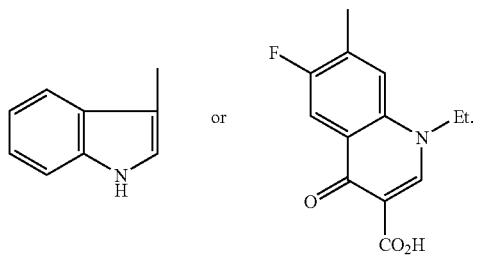

A third aspect of the present invention provides a method of treating a condition which can be alleviated by antagonism of a 5-$HT_{2B}$ receptor, which method comprises administering to a patient in need of treatment an effective amount of a compound of formula I, or a pharmaceutically acceptable salt thereof.

Conditions which can be alleviated by antagonism of a 5-$HT_{2B}$ receptor are discussed above, and particularly include disorders of the GI tract.

It is preferred that the compounds described above are selective as against 5-$HT_{2A}$ and 5-$HT_{2C}$ receptors.

Definitions $C_{1-6}$ alkyl group: The term "$C_{1-6}$ alkyl", as used herein, pertains to a monovalent moiety obtained by removing a hydrogen atom from a carbon atom of a non-cyclic hydrocarbon compound having from 1 to 6 carbon atoms, and which may be saturated or unsaturated.

Examples of saturated $C_{1-6}$ alkyl groups include methyl ($C_1$); ethyl ($C_2$); propyl ($C_3$), which may be linear (n-propyl) or branched (iso-propyl); butyl ($C_4$), which may be linear (n-butyl) or branched (iso-butyl, sec-butyl and tert-butyl); pentyl ($C_5$), which may be linear (n-pentyl, amyl) or branched (iso-pentyl, neo-pentyl); hexyl ($C_6$), which may be linear (n-hexyl) or branched.

Examples of unsaturated $C_{1-6}$ alkyl groups, which may be referred to as $C_{1-6}$ alkenyl (if they included a double bond) or $C_{1-6}$ alkynyl (if they include a triple bond) groups, include ethenyl (vinyl, —CH=$CH_2$), ethynyl (ethinyl, —C≡CH), 1-propenyl (—CH=CH—$CH_3$), 2-propenyl (allyl, —CH—CH=$CH_2$), 2-propynyl (propargyl, —$CH_2$—C≡CH), isopropenyl (—C($CH_3$)=$CH_2$), butenyl ($C_4$), pentenyl ($C_5$), and hexenyl ($C_6$).

$C_{3-7}$ Cycloalkyl: The term "$C_{3-7}$ cycloalkyl", as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 ring atoms Examples of saturated cycloalkyl groups include, but are not limited to, those derived from: cyclopropane ($C_3$), cyclobutane ($C_4$), cyclopentane ($C_5$), cyclohexane ($C_6$), and cycloheptane ($C_7$).

Examples of unsaturated cylcoalkyl groups include, but are not limited to, those derived from: cyclobutene ($C_4$), cyclopentene ($C_5$), cyclohexene ($C_6$), and cycloheptene ($C_7$).

$C_{3-7}$ cycloalkyl-$C_{1-4}$ alkyl: The term "$C_{3-7}$ cycloalkyl-$C_{1-4}$ alkyl", as used herein, pertains to a monovalent moiety obtained by removing a hydrogen atom from a carbon atom of a non-cyclic hydrocarbon compound having from 1 to 4 carbon atoms ($C_{1-4}$ alkyl), which may be saturated or unsaturated, which itself is substituted by a $C_{3-7}$ cycloalkyl group.

Examples of $C_{3-7}$ cycloalkyl-$C_{1-4}$ alkyl groups include, but are not limited to, those derived from: cyclohexylethane ($C_6$-$C_2$) and cyclopentylpropene ($C_5$-$C_3$).

Phenyl-$C_{1-4}$ alkyl: The term "phenyl-$C_{1-4}$ alkyl", as used herein, pertains to a monovalent moiety obtained by removing a hydrogen atom from a carbon atom of a non-cyclic hydrocarbon compound having from 1 to 4 carbon atoms ($C_{1-4}$ alkyl), which may be saturated or unsaturated, which itself is substituted by a phenyl group ($C_6H_5$—).

Examples of phenyl-$C_{1-4}$ alkyl groups include, but are not limited to, benzyl (phenyl-$CH_2$—) and those derived from: phenylethane (phenyl-$C_2$) and phenylpropene (phenyl-$C_3$).

$C_{5-7}$ Heterocyclyl: The term "$C_{5-7}$ heterocyclyl", as used herein, pertains to a monovalent moiety obtained by removing a hydrogen atom from a ring atom of a heterocyclic compound, which moiety has from 5 to 7 ring atoms, of which from 1 to 4 are ring heteroatoms. In particular, when $R^2$ and $R^3$ together with the nitrogen atom to which they are attached form a $C_{5-7}$ heterocyclic ring, at least one ring atom will be nitrogen.

Examples of $C_{5-7}$ heterocyclyl groups having at least one nitrogen atom, include, but are not limited to, those derived from:

$N_1$: pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$N_1O_1S_1$: oxathiazine ($C_6$).

$C_{9-14}$ Aryl: The term "$C_{9-14}$ aryl", as used herein, pertains to a monovalent moiety obtained by removing a hydrogen atom from an aromatic ring atom of an aromatic compound with at least two fused rings, which moiety has from 9 to 14 ring atoms. Preferably, each ring has from 5 to 7 ring atoms.

The ring atoms may be all carbon atoms, as in "carboaryl groups" (e.g. $C_{9-14}$ carboaryl).

Examples of carboaryl groups include, but are not limited to, those derived from naphthalene ($C_{10}$), azulene ($C_{10}$), anthracene ($C_{14}$) and phenanthrene ($C_{14}$).

Examples of aryl groups which comprise fused rings, at least one of which is an aromatic ring, include, but are not limited to, groups derived from indene ($C_9$), isoindene ($C_9$) tetralin ($C_{10}$) and fluorene ($C_{13}$).

Alternatively, the ring atoms may include one or more heteroatoms, as in "heteroaryl groups" (e.g. $C_{9-14}$ heteroaryl).

Examples of heteroaryl groups, include, but are not limited to:

$C_9$ heteroaryl groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g. adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiophene ($S_1$), benzothiazole ($N_1S_1$), benzothiadiazole ($N_2S$);

$C_{10}$ heteroaryl groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ heteroaryl groups (with 2 fused rings) derived from benzoazepine ($N_1$), 5-oxa-9-aza-benzocycloheptene ($N_1O_1$);

$C_{13}$ heteroaryl groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ heteroaryl groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above described $C_{9-14}$ aryl group includes the radical formed by removal of a hydrogen atom from any of the possible aromatic ring atoms. The groups formed by this removal can be described by the number of the ring atom from which the hydrogen is removed, if there is more than one possibility. The carboaryl groups derived from, for example, naphthalene ($C_{10}$) can be either napth-1-yl or nath-2-yl; and from azulene ($C_{10}$) can be azul-1-yl, azul-2-yl, azul-4-yl, azul-5-yl and azul-6-yl. The heteroaryl groups derived, for example, from isoquinoline can be isoquinol-x-yl (x-isoquinolyl), where x can be 1, 3, 4, 5, 6, 7 or 8.

The phrase "optionally substituted", as used herein, pertains to a parent group, as above, which may be unsubstituted or which may be substituted by one of the following substituent groups:

$C_{1-20}$ alkyl group: The term "$C_{1-20}$ alkyl", as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl and cycloalkyl discussed below.

In this context, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl," as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), n-undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include isopropyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl", as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of saturated cycloalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$ alkenyl, $C_{2-7}$ alkenyl, $C_{2-20}$ alkenyl.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (—C($CH_3$)=$CH_2$), butenyl ($C_4$), pentenyl ($C_5$), and hexenyl ($C_6$).

Examples of unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$ alkynyl, $C_{2-7}$ alkynyl, $C_{2-20}$ alkynyl.

Examples of unsaturated alkynyl groups include, but are not limited to, ethynyl (ethinyl, —C≡CH) and 2-propynyl (propargyl, —$CH_2$—C≡CH).

$C_{3-20}$ heterocyclyl group: The term "$C_{3-20}$ heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$ heterocyclyl, $C_{3-7}$ heterocyclyl, $C_{5-7}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R$^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

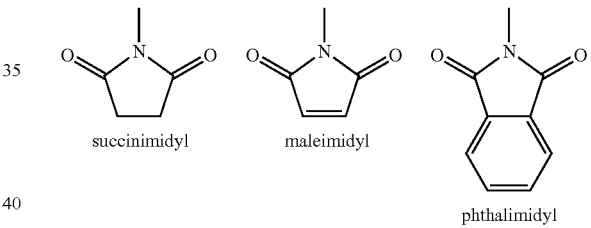

succinimidyl     maleimidyl     phthalimidyl

Thioamido (thiocarbamyl): —C(=S)NR$^1$R$^2$, wherein R$^1$ and R$^2$ are independently amino substituents, as defined for amino groups. Examples of thioamido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

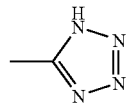

Amino: —NR¹R², wherein R¹ and R² are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R¹ and R², taken together with the nitrogen atom to which they are attached, form a heterocyclic ring having from 4 to 8 ring atoms. Amino groups may be primary (—NH₂), secondary (—NHR¹), or tertiary (—NHR¹R²), and in cationic form, may be quaternary (—⁺NR¹R²R³). Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR₂, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH₂, —C(=NH)NMe₂, and —C(=NMe)NMe₂.

Nitro: —NO₂.

Nitroso: —NO.

Cyano (nitrile, carbonitrile): —CN.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH₃ and —SCH₂CH₃.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a $C_{1-7}$alkyl group, a $C_{3-20}$heterocyclyl group, or a $C_{5-20}$aryl group, preferably a $C_{1-7}$alkyl group, including, for example, a fluorinated or perfluorinated $C_{1-7}$alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂C₄F₉ (nonaflyl), —S(=O)₂CH₂CF₃ (tresyl), —S(=O)₂CH₂CH₂NH₂ (tauryl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO₂H.

Sulfonic acid (sulfo): —S(=O)₂OH, —SO₃H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH₃ (methoxysulfinyl; methyl sulfinate) and —S(=O)OCH₂CH₃ (ethoxysulfinyl; ethyl sulfinate).

Sulfonate (sulfonic acid ester): —S(=O)₂OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)₂OCH₃ (methoxysulfonyl; methyl sulfonate) and —S(=O)₂OCH₂CH₃ (ethoxysulfonyl; ethyl sulfonate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH₃ and —OS(=O)CH₂CH₃.

Sulfonyloxy: —OS(=O)₂R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)₂CH₃ (mesylate) and —OS(=O)₂CH₂CH₃ (esylate).

Sulfate: —OS(=O)₂OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)OCH₃ and —SO(=O)₂OCH₂CH₃.

Sulfamyl (sulfamoyl; sulfinic acid amide; sulfinamide): —S(=O)NR¹R², wherein R¹ and R² are independently amino substituents, as defined for amino groups. Examples of sulfamyl groups include, but are not limited to, —S(=O)NH₂, —S(=O)NH(CH₃), —S(=O)N(CH₃)₂, —S(=O)NH(CH₂CH₃), —S(=O)N(CH₂CH₃)₂, and —S(=O)NHPh.

Sulfonamido (sulfinamoyl; sulfonic acid amide; sulfonamide): —S(=O)₂NR¹R², wherein R¹ and R² are independently amino substituents, as defined for amino groups. Examples of sulfonamido groups include, but are not limited to, —S(=O)₂NH₂, —S(=O)₂NH(CH₃), —S(=O)₂N(CH₃)₂, —S(=O)₂NH(CH₂CH₃), —S(=O)₂N(CH₂CH₃)₂, and —S(=O)₂NHPh.

Sulfamino: —NR¹S(=O)₂OH, wherein R¹ is an amino substituent, as defined for amino groups. Examples of sulfamino groups include, but are not limited to, —NHS(=O)₂OH and —N(CH₃)S(=O)₂OH.

Sulfonamino: —NR¹S(=O)₂R, wherein R¹ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)₂CH₃ and —N(CH₃)S(=O)₂C₆H₅.

Sulfinamino: —NR¹S(=O)R, wherein R¹ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH₃ and —N(CH₃)S(=O)C₆H₅.

The above listed substituent groups, may themselves be further substituted, where appropriate, by one or more of themselves.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO⁻), a salt or solvate thereof, as well as conventional protected forms. Similarly, a reference to an amino group includes the protonated form (—N⁺HR¹R²), a salt or solvate of the amino group, for example, a hydrochloride salt, as well as conventional protected forms of an amino group. Similarly, a reference to a hydroxyl group also includes the anionic form (—O⁻), a salt or solvate thereof, as well as conventional protected forms of a hydroxyl group.

Isomers, Salts, Solvates and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

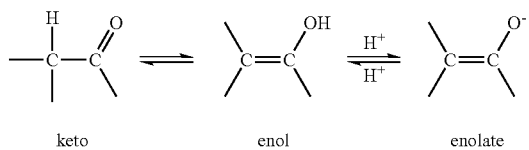

keto        enol        enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19, which is herein incorporated by reference.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999), which is herein incorporated by reference.

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$)

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Suitable dose ranges will typically be in the range of from 0.01 to 20 mg/kg/day, preferably from 0.1 to 10 mg/kg/day.

Compositions and Their Administration

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th, Edition, 1975. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Synthesis Methods

Compounds of formula I where $R^4$ is an optionally substituted $C_{9-14}$ aryl group and at least one of $R^2$ and $R^3$ are hydrogen, and where $R^1$ is hydrogen, can be synthesised according to the route disclosed by Cockerill (Cockerill, A. F., et al., *Synthesis*, 1976, 591-593, which is herein incorporated by reference).

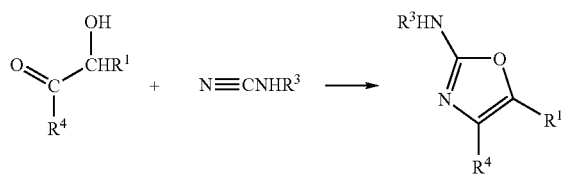

In this method the 2-amino oxazole is produced by the condensation of the appropriate α-hydroxy ketone with cyanamide or alkylcyanamide, which reaction can be carried out in aqueous solution or in the presence of a mineral acid or a base catalyst (e.g. N,N-dimethylformamide).

If, in the starting material, $R^1$ is not H, then the product of the method is a compound of the following formula II:

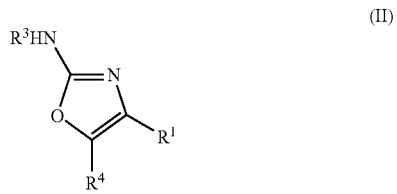

wherein $R^4$ is an optionally substituted $C_{9-14}$ aryl group.

Without wishing to be bound by theory, this product results from the reaction of the tautomeric form of the starting material:

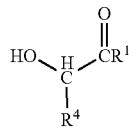

The two tautometric forms of the starting material exist in equilibrium, which when $R^1$ is H, is almost completely in favour of the α-hydroxy ketone shown in the first scheme above. When $R^1$ is not H, then the starting material appears to exist as a mixture, but the reaction with cyanamide/alkylcyanamide only results in the compound of formula II being isolated.

The starting α-hydroxyketones can be synthesised via α-bromo and α-acetoxy intermediates, some of which are commercially available, from the parent ketones.

The substitution on the 2-amino group can be introduced using a substituent on the cyanamide, or may be introduced later in the reaction scheme, again with, if necessary, protection of other functional groups in the molecule (see, for example, Examples 9 and 15 below)

Compounds of formula Ia where $R^4$ is an optionally substituted $C_{9-14}$ aryl group and both $R^2$ and $R^3$ are not hydrogen can be synthesised according to a modification of the route disclosed by Gompper (Gompper, R., and Christmann, O., *Chem. Ber.* 92, 1944-1949 (1959), which is herein incorporated by reference).

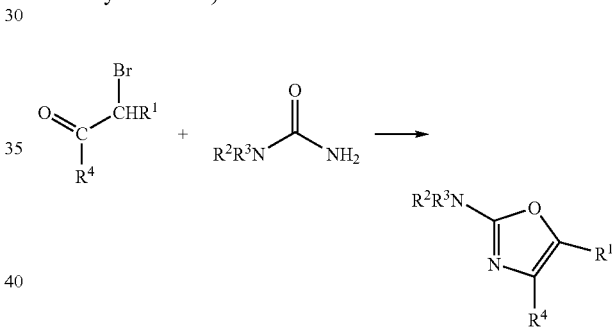

In this method the 2-amino oxazole is produced by the condensation of the appropriate α-bromo ketone with 1,1-dialkyl urea, which reaction is carried out in an organic solvent.

The 5-substituent on the oxazole ring is present in the starting material as the alkyl chain of the α-bromo alkylarylketone, which can be obtained from the parent alkylarylketone if necessary.

This route can be used for compounds of formula I where $R^4$ is an optionally substituted $C_{9-14}$ aryl group and at least one of $R^2$ and $R^3$ are hydrogen, but is less preferred for these compounds.

The starting ketones for both routes are either commercially available or accessible by, for example, Grignard reactions on the corresponding nitriles or Friedal Crafts reaction of substituted aryls.

A further method of preparing compounds of formula I where $R^4$ is an optionally substituted $C_{9-14}$ aryl group is by a palladium catalysed coupling reaction of a 2-amino-4-substituted oxazole with an aryl boronic acid, or derivative thereof. The 4-sustituent on the oxazole ring may typically be a halogen, such as bromo, iodo or chloro, or a group such as trifluoromethanesulfonate or a phophate ester. The aryl boronic acid may also be replaced by certain magnesium, tin or zinc containing organometallic reagents. For example, a 2-amino-4-bromo-oxazole may be reacted with an aryl boronic acid derivative in an aqueous solvent, for example a mixture of ethanol, water and dimethoxyethane, containing a palladium catalyst such as tetrakis(triphenylphosphine)palladium(0) and an inorganic base such as sodium carbonate. The reaction is carried out by heating at about 80-90° for several hours.

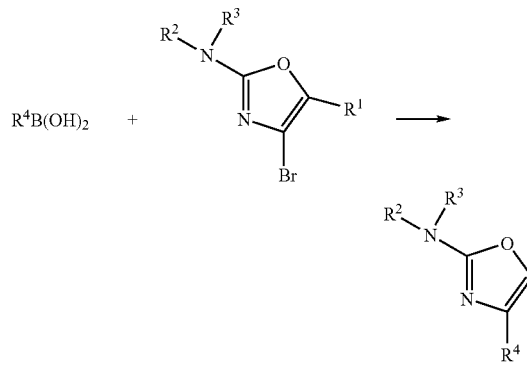

Alternatively, the boronic acid residue, or equivalent, may be on the 4-position of the oxazole ring and the halogen, or equivalent, on the aryl group.

This route is equally applicable to compounds of formula I where $R^1$ is an optionally substituted $C_{9-14}$ aryl group, where the 2-amino-4-bromo-oxazole is replaced with a 2-amino-5-bromo-oxazole:

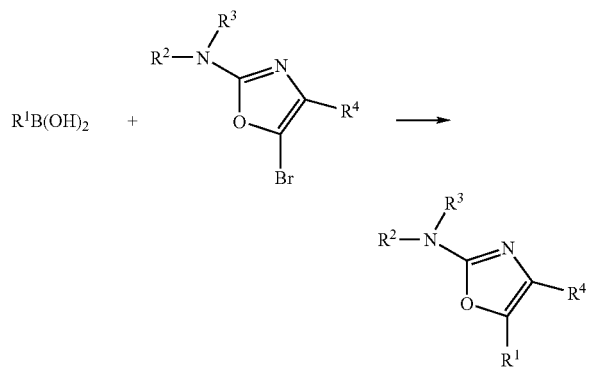

This route may be varied in the same way as described above.

In any of the above routes, any substitution on the $C_{9-14}$ aryl group is preferably present in the relevant starting material, but could be introduced later in the reaction scheme, with, if necessary, appropriate protection of other functional groups present in the molecule (see, for example, Examples 11A, 11B, 12, 13 and 14).

In a similar fashion, the $R^1/R^4$ group which is not the $C_{9-14}$ aryl group may be the subject of further reactions to provide alternative substituent pattens.

Preferences

The following preferences may be combined with one another, and may be different for each aspect of the present invention.

The optional substituents for $R^1$, $R^2$, $R^3$ and $R^4$ are preferably independently selected from halo, hydroxy, alkoxy (more preferably $C_{1-4}$ alkoxy), amino (more preferably $NH_2$, $C_{1-4}$ alkyl amino, $C_{1-4}$ dialkyl amino), and amido (more preferably $CONH_2$, $C_{1-4}$ alkyl amido, $C_{1-4}$ dialkyl amido)

It is preferred that $R^1$ is the optionally substituted $C_{9-14}$ aryl group.

One of $R^1$ and $R^4$ is preferably selected from H and optionally substituted $C_{1-6}$ alkyl and $C_{3-7}$ cycloalkyl, more preferably H and optionally substituted $C_{1-6}$ alkyl. Especially preferred are H, and $C_{1-4}$ alkyl (e.g. methyl, iso-propyl). In some embodiments the group may be unsubstituted, but when the group is substituted, preferred substituent groups include halo, hydroxy, and amino. Most preferably, one of $R^1$ and $R^4$ is H or methyl.

In some embodiments it is preferred that both $R^2$ and $R^3$ are substituted, and in other embodiments that only one or neither of $R^2$ and $R^3$ are substituted. Each of $R^2$ and $R^3$ are preferably independently selected from H, R, R', where R and R' are as defined above, and more preferably selected from H and R. R is preferably an optionally substituted $C_{1-4}$ alkyl group. The preferred substituents for R and R' include halo, hydroxy, amino and acetyl.

The other of $R^1$ and $R^4$ is preferably an optionally substituted $C_{9-14}$ carboaryl group, for example, naphth-1-yl, naphth-2-yl, anthracen-1-yl, anthracen-2-yl, anthracen-9-yl, phenanthren-1-yl, phenanthren-2-yl, phenanthren-3-yl and phenanthren-4-yl, phenanthren-9-yl. Of these napth-1-yl and napth-2-yl are preferred, with napthy-1-yl being most preferred. Other preferred $R^4$ groups include benzo[b]thiophen-2-yl, benzo[b]thiophen-4-yl and benzo[1,4]dioxin-5-yl.

Preferred substituent groups for the $C_{9-14}$ aryl group include halo, hydroxy, $C_{1-4}$ alkoxy, cyano, amino, amido and $C_{1-4}$ alkyl, of which hydroxy, and $C_{1-4}$ alkoxy are more preferred. It is also preferred that the $C_{9-14}$ aryl group bears no oxo substituents.

If the $C_{9-14}$ aryl group is a naphth-1-yl group, preferred substituent positions are 2, 4 and 7, with 2 being most preferred. The preferred substituents at the 2-position are hydroxy, $C_{1-4}$ alkyl and $C_{1-4}$ alkoxy, with $C_{1-4}$ alkoxy (e.g. methoxy and ethoxy) being most preferred.

Particularly preferred compounds include: 2-amino-4-(napthy-1-yl)oxazole (1), 2-methylamino-4-(napth-1-yl)oxazole (2), 2-amino-4-methyl-5-(napth-1-yl)oxazole (3), 2-amino-4-(4'-fluoronaphth-1-yl)oxazole (4), 2-amino-4-(7'-bromonaphth-1-yl)oxazole (5), 2-amino-4-(2'-methyl-naphth-1-yl)oxazole (6), 2-amino-4-isopropyl-5-(naphth-1-yl)oxazole (7), 2-dimethylamino-4-(naphth-1-yl)oxazole (8), 2-acetylamino-4-(naphth-1-yl)oxazole (9), 4-(2-ethoxy-naphthalen-1-yl)-oxazol-2-ylamine (10), 4-(4-methoxy-naphthalen-1-yl)-oxazol-2-ylamine (11), 4-(2-benzyloxy-naphthalen-1-yl)-oxazol-2-ylamine (12), 4-(3-methyl-benzo[b]thiophen-2-yl)-oxazol-2-ylamine (13), 4-(2,3-dihydro-benzo[1,4]dioxin-6-yl)-oxazol-2-ylamine (14), 4-benzo[b]thiophen-4-yl-oxazol-2-ylamine (15), 4-naphthalen-2-yl-oxazol-2-ylamine (16), 4-(2-methoxy-naphthalen-1-yl)-oxazol-2-ylamine (17), 4-(1-methoxy-naphthalen-2-yl)-oxazol-2-ylamine (18), 4-(5-bromo-naphthalen-1-yl)-oxazol-2-ylamine (19), 4-(7-carbonitrile-naphthalen-1-yl)-oxazol-2-ylamine (20), 4-(5-carbonitrile-naphthalen-1-yl)-oxazol-2-ylamine (21), 1-(2-amino-oxazol-4-yl)-naphthalen-2-ol (22), [1-(2-amino-oxazol-4-yl)-naphthalen-2-yloxy]-acetic acid methyl ester (23), 8-(2-amino-oxazol-4-yl)-naphthalene-2-carboxylic acid amide (24), N-[4-(2-methoxy-naphthalen-1-yl)-oxazol-2-yl]-acetamide (25), 5-(2-methoxy-naphthalen-1-yl)-4-methyl-oxazol-2-ylamine (26), acetic acid 2-amino-5-naphthalen-1-yl-oxazol-4-ylmethyl ester (28), (2-amino-5-naphthalen-1-yl-oxazol-4-yl)- methanol (29), 5-Methyl-4-naphthalen-1-yl-oxazol-2-ylamine (30) and 2-amino-4-isopropyl-5-(4'-fluoronaphth-1-yl)oxazole (31).

The most preferred compounds are 2-amino-4-methyl-5-(napth-1-yl)oxazole (3), 2-amino-4-(2'-methylnaphth-1-yl)oxazole (6), 2-amino-4-isopropyl-5-(naphth-1-yl)oxazole (7), 4-(2-methoxy-naphthalen-1-yl)-oxazol-2-ylamine (17) and 2-amino-4-isopropyl-5-(4'-fluoronaphth-1-yl)oxazole (31).

The selectivity of the compound for antagonising 5-$HT_{2B}$ receptors over 5-$HT_{2A}$ and/or 5-$HR_{2C}$ receptors can be quantified by dividing the Ki for 5-$HT_{2B}$ (see below) by the Ki for 5-$HT_{2A/2C}$ (see below). The resulting ratio is preferably 10 or more, more preferably 100 or more.

The following examples illustrate the invention.

EXAMPLE 1

Synthesis of 2-amino-4-(naphth-1-yl)oxazole (1)

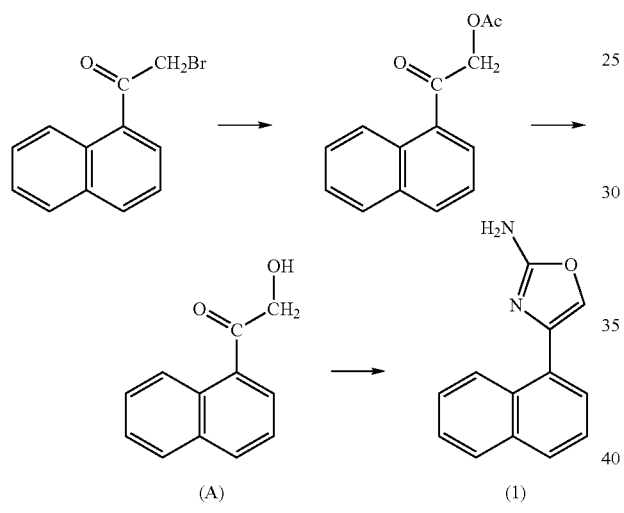

a. Synthesis of 1-(α-acetoxy)acetylnaphthalene 1-(α-Bromo)acetylnaphthalene (10.3 g) and sodium acetate (3.3 g) were boiled under reflux in anhydrous ethanol (55 ml) for 16 hours. The mixture was cooled and partitioned-between dichloromethane and water. The organic layer was separated, washed with water, brine, dried with sodium sulphate, filtered and evaporated in vacuo. The title compound was obtained as an oil (5.4 g) following silica gel column chromatography of the residue in 20-50% ethyl acetate in petroleum ether.

$^1$H NMR (CDCl$_3$, δ): 2.3 (3H, s); 5.3 (2H, s); 7.5-7.7 (3H, m); 7.9 (2H, t); 8.1 (1H, d); 8.65 (1H, d)

b. Synthesis of 1-(α-hydroxy)acetylnaphthalene (A)

A mixture of 1-(α-acetoxy)acetylnaphthalene (5.4 g), IMS (60 ml) and hydrochloric acid (1M; 50 ml) was boiled under reflux for 6 hours. The mixture was cooled and partitioned between ethyl acetate and water. The organic layer was separated, washed with water, brine, dried with sodium sulphate, filtered and evaporated in vacuo to afford the title compound as an oil (4.3 g).

$^1$H NMR (CDCl$_3$, δ): 3.7 (1H, broad s); 4.95 (2H, s); 7.55-7.9 (5H, m); 8.1 (1H, d); 8.9 (1H, d)

c. Synthesis of 2-amino-4-(naphth-1-yl)oxazole (1)

1-(α-Hydroxy)acetylnaphthalene (A) (4.2 g) and cyanamide (1.3 g) were boiled to reflux in anhydrous ethanol for 3 days. The mixture was cooled and evaporated in vacuo. The residue was dissolved in ethyl acetate and washed with 1M hydrochloric acid. The aqueous layer was back-extracted once with ethyl acetate and the combined organic extracts were washed with brine, dried with sodium sulphate, filtered and evaporated in vacuo. The title compound (1) (0.4 g; m.p. 155-162° C.) was obtained following silica gel column chromatography of the residue in ethyl acetate.

$^1$H NMR (d$_6$-DMSO, δ): 6.9 (2H, broad s); 7.25 (1H, s); 7.5-7.7 (4H, m); 7.85 (1H, d); 7.95 (1H, m); 8.3 (1H, m) Mass spectrum (m/z): 211 (M+H)$^+$ Microanalysis: C expected 74.27 found 73.87; H expected 4.79 found 5.15; N expected 13.32 found 12.60

The aqueous acid wash was basified with 15% sodium hydroxide solution to pH 10 and extracted with ethyl acetate. The organic layer was separated, washed with brine, dried with sodium sulphate, filtered and evaporated in vacuo. The residue was re-crystallized from chloroform to yield a further quantity of the title compound (1) (0.6 g).

EXAMPLE 2

Synthesis of 2-methylamino-4-(naphth-1-yl)oxazole (2)

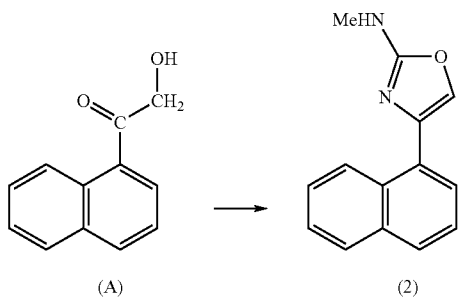

To a suspension of cyanogen bromide (4.5 g) and sodium carbonate (9.0 g) in anhydrous tetrahydrofuran (16 ml), cooled to between −10° C. and −20° C., was added methylamine (2M solution in tetrahydrofuran; 20 ml), keeping the temperature below −5° C. After addition, the mixture was stirred for a further 90 minutes at −15° C. then allowed to warm up to 5° C. and filtered. An aliquot (8 ml) of the filtrate was removed and added to 1-(α-Hydroxy)acetylnaphthalene (A)(1.0 g). To the resultant solution was added water (8 ml) followed by sodium hydroxide solution (2M; 0.5 ml). The mixture was left overnight, added to brine and extracted twice with dichloromethane. The combined organic layers were dried with sodium sulphate, filtered and evaporated in vacuo. Silica gel column chromatography of the residue in chloroform followed by crystallisation from ethyl acetate yielded the title compound (2) (0.12 g; m.p. 164-166° C.).

$^1$H NMR (CDCl$_3$, δ): 3.05 (3H, d); 5.1 (1H, broad s); 7.4 (1H, s); 7.5 (3H, m); 7.75 (2H, d); 7.9 (2H, m); 8.4 (1H, m) Mass spectrum (m/z): 225 (M+H)$^+$ Microanalysis: C expected 74.98 found 74.70; H expected 5.39 found 5.40; N expected 12.49 found 12.35

EXAMPLE 3

Synthesis of 2-amino-4-methyl-5-(naphth-1-yl)oxazole (3)

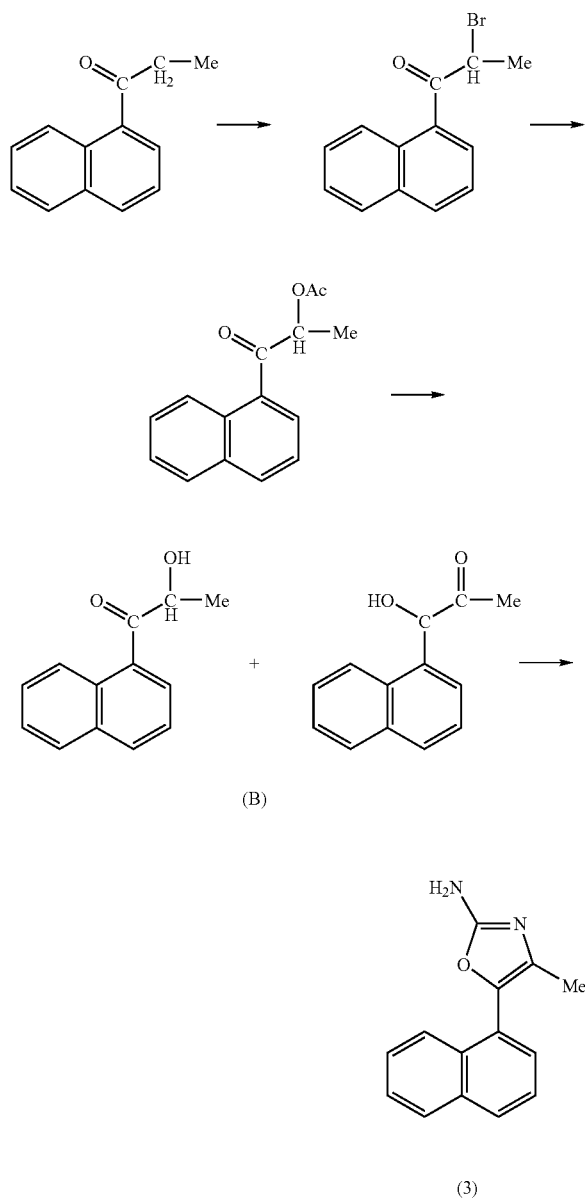

(3)

a. Synthesis of 2-bromo-1-(naphth-1-yl)-1-propanone

To a solution of 1-(naphth-1-yl)-1-propanone (4.0 g) in anhydrous tetrahydrofuran (50 ml) was added phenyltrimethylammonium tribromide (8.0 g). The resulting mixture was stirred overnight at room temperature then partitioned between petroleum ether and aqueous sodium carbonate solution. The organic layer was separated, washed with water, brine, dried with sodium sulphate, filtered and evaporated in vacuo to yield crude 2-bromo-1-(naphth-1-yl)-1-propanone (5.7 g).

$^1$H NMR (CDCl$_3$, δ): 2.0 (3H, d); 4.9 (1H, q); 7.45-7.7 (3H, m); 7.9 (2H, t); 8.05 (1H, d); 8.45 (1H, d)

b. Synthesis of 2-acetoxy-1-(naphth-1-yl)-1-propanone 2-bromo-1-(napth-1-yl)-1-propanone (2 g) and sodium acetate (0.63 g) were boiled under reflux in anhydrous ethanol (10 ml) for 16 hours. The mixture was cooled and evaporated in vacuo. The residue was partitioned between ethyl acetate and water. The organic layer was separated, washed with water, brine, dried with sodium sulphate, filtered and evaporated in vacuo. The title compound was obtained as an oil (0.75 g) following silica gel column chromatography of the residue in 50% dichloromethane in petroleum ether.

$^1$H NMR (CDCl$_3$, δ): 1.5 (3H, d); 2.2 (3H, s); 6.0 (1H, q) 7.5-7.7 (3H, m); 7.85-8.05 (3H, m); 8.4 (1H, d)

c. Synthesis of 2-amino-4-methyl-5-(naphth-1-yl)oxazole

A mixture of 2-acetoxy-1-(naphth-1-yl)-1-propanone (2.6 g), IMS (30 ml) and hydrochloric acid (1M; 22 ml) was boiled under reflux for 4 hours. The mixture was cooled, added to brine and extracted twice with dichloromethane. The combined organic extracts were dried with sodium sulphate, filtered and evaporated in vacuo to afford a mixture of crude 2-hydroxy-1-naphthalen-1-yl-propan-1-one and 1-hydroxy-1-naphthalen-1-yl-propan-1-one (B) as an oil (2.2 g). A portion of this material (0.5 g) was dissolved in tetrahydrofuran (2 ml) to which was added cyanamide (0.11 g), water (2 ml) and sodium hydroxide solution (2M; 0.25 ml). The mixture was stirred vigorously for 16 hours then tetrahydrofuran was added (10 ml). The mixture was heated to 40° C. for 30 minutes, cooled and left for a further 6 hours. Brine was added and the mixture was extracted twice with dichloromethane. The combined organic extracts were dried with sodium sulphate, filtered and evaporated in vacuo. The title compound (3) (0.13 g; m.p. 187-189° C.) was obtained following silica gel column chromatography of the residue in 50% ethyl acetate in petroleum ether.

$^1$H NMR (d$_6$-DMSO, δ): 2.0 (3H, s); 6.7 (2H, broad s); 7.5 (4H, m); 7.95 (3H, m) Mass spectrum (m/z): 225 (M+H)$^+$ Microanalysis: (for 0.1 moles of water) C expected 74.38 found 74.68; H expected 5.44 found 5.56; N expected 12.39 found 12.03

EXAMPLE 4

Synthesis of 2-amino-4-(4'-fluoronaphth-1-yl)oxazole (4)

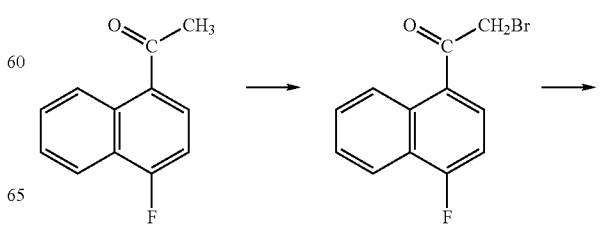

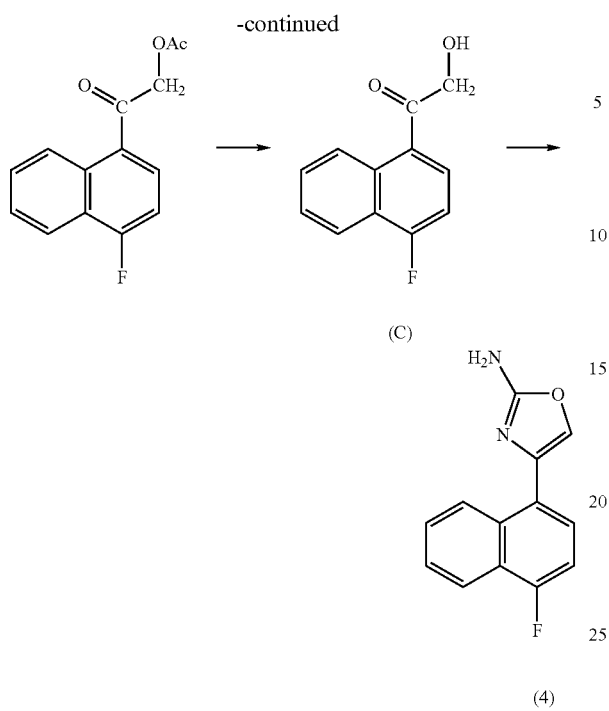

(C)

(4)

a. Synthesis of 1-(α-acetoxy)acetyl-4-fluoronaphthalene

To a solution of 1-acetyl-4-fluoronaphthalene (2.1 g) in anhydrous tetrahydrofuran (20 ml) was added phenyltrimethylammonium tribromide (4.2 g). The resulting mixture was stirred overnight at room temperature then partitioned between petroleum ether and aqueous sodium carbonate solution. The organic layer was separated, washed with water, brine, dried with sodium sulphate, filtered and evaporated in vacuo to yield crude 1-(α-bromo)acetyl-4-fluoronaphthalene (4.1 g). Sodium acetate (4.0 g) and anhydrous ethanol (100 ml) were added and the resulting mixture was boiled under reflux in anhydrous ethanol (100 ml) for 20 hours. The mixture was cooled, added to water and extracted three times with dichloromethane. The combined organic layers were dried with sodium sulphate, filtered and evaporated in vacuo. The title compound (1.25 g) was obtained following re-crystallisation of the residue from aqueous IMS.

$^1$H NMR (CDCl$_3$, δ): 2.3 (3H, s); 5.3 (2H, s); 7.15 (1H, m); 7.65 (2H, m); 7.9 (1H, m); 8.15 (1H, d); 8.75 (1H, d)

b. Synthesis of 2-amino-4-(4'-fluoronaphth-1-yl)oxazole

A mixture of 1-(α-acetoxy)acetyl-4-fluoronaphthalene (1.1 g), IMS (20 ml) and hydrochloric acid (1M; 20 ml) was boiled under reflux for 20 hours. The mixture was cooled and evaporated in vacuo. Chromatography of the residue in 50% chloroform in petroleum ether afforded crude 1-(α-hydroxy)acetyl-4-fluoronaphthalene (C) (0.55 g). Cyanamide (0.15 g) and anhydrous ethanol (5 ml) were added and the resulting mixture was boiled under reflux for 2 days. The mixture was cooled and evaporated in vacuo. The title compound (4) (0.1 g; m.p. 171-174° C.) was obtained following silica gel column chromatography of the residue in 50% ethyl acetate in petroleum ether.

$^1$H NMR (d$_6$-DMSO, δ): 6.9 (2H, broad s); 7.2 (1H, s); 7.4 (1H, m); 7.6 (1H, m); 7.7 (2H, m); 8.1 (1H, m); 8.35 (1H, m) Mass spectrum (m/z): 229 (M+H)$^+$

EXAMPLE 5

Synthesis of 2-amino-4-(7'-bromonaphth-1-yl)oxazole (5)

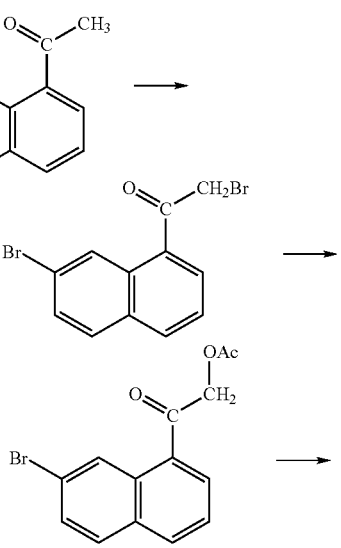

(D)

(5)

a. Synthesis of 1-(α-acetoxy)acetyl-7-bromonaphthalene

To a solution of 1-acetyl-7-bromonaphthalene (5 g) in anhydrous tetrahydrofuran (50 ml) was added phenyltrimethylammonium tribromide (8.4 g). The resulting mixture was stirred overnight at ambient temperature then partitioned between petroleum ether and water. The organic layer was separated, washed with water, brine, dried with sodium sulphate, filtered and evaporated in vacuo to yield crude 1-(α-bromo)acetyl-7-bromonaphthalene (7 g). Sodium acetate (2.35 g) and anhydrous ethanol (30 ml) were added and the resulting mixture was boiled under reflux for 20 minutes. The mixture was cooled, evaporated in vacuo and partitioned between water and chloroform. The organic layer was separated, dried with sodium sulphate, filtered and evaporated in vacuo. The title compound was obtained (1.1 g) following re-crystallisation of the residue from ethyl acetate. Silica gel column chromatography of the evaporated mother liquors in 50% dichloromethane in petroleum ether afforded a further 2 g of the title compound.

$^1$H NMR (CDCl$_3$, δ): 2.25 (3H, s); 5.3 (2H, s); 7.5-8.1 (5H, m); 8.9 (1H, broad s)

b. Synthesis of 2-amino-4-(7'-bromonaphth-1-yl)oxazole

A mixture of 1-(α-acetoxy)acetyl-7-bromonaphthalene (3 g), IMS (100 ml) and hydrochloric acid (2M; 25 ml) was boiled under reflux for 70 minutes. The mixture was cooled, evaporated and the residue was partitioned between ethyl acetate and water. The organic layer was separated, washed with water, brine, dried with sodium sulphate, filtered and evaporated in vacuo. The intermediate 1-(α-hydroxy)acetyl-7-bromonaphthalene (D) was obtained following silica gel column chromatography of the residue in dichloromethane (4.3 g).

1-(α-Hydroxy)acetyl-7-bromonaphthalene (D) (2.2 g) and cyanamide (0.44 g) were boiled to reflux in anhydrous ethanol for 2 days. The mixture was cooled and evaporated in vacuo. The residue was partitioned between chloroform and water. The organic layer was separated, dried with sodium sulphate, filtered and evaporated in vacuo. The title compound (5) (0.35 g; m.p. 189-190° C.) was obtained following column chromatography of the residue on silica gel in 4% methanol in chloroform and re-crystallisation from ethyl acetate.

$^1$H NMR (CDCl$_3$/d$_6$-DMSO, δ): 5.7 (2H, broad s); 7.0 (1H, s); 7.4-7.75 (5H, m); 8.4 (1H, broad s). Mass spectrum (m/z): 289, 290 (M+H)$^+$ Microanalysis: C expected 54.00 found 53.96; H expected 3.14 found 3.13; N expected 9.69 found 9.51.

EXAMPLE 6

Synthesis of 2-amino-4-(2'-methylnaphth-1-yl)oxazole (6)

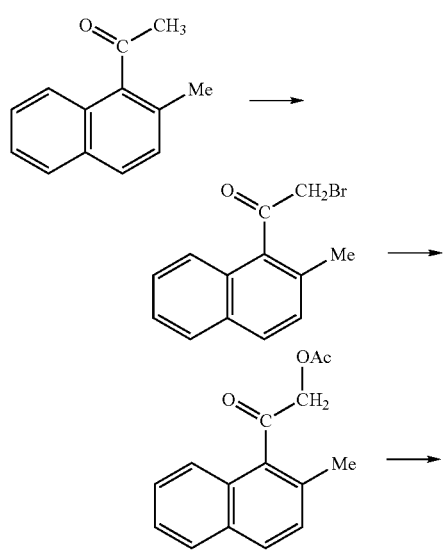

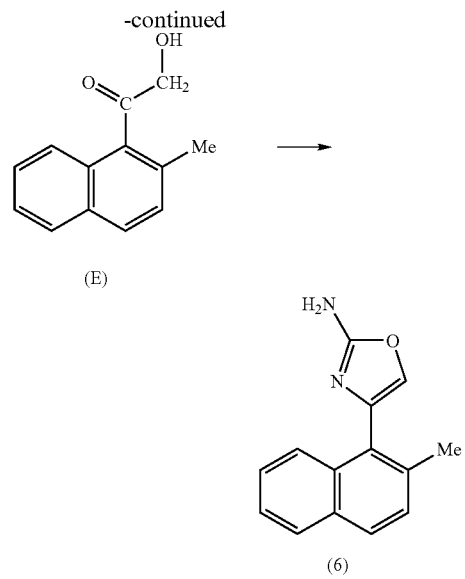

a. Synthesis of 1-(α-bromo)acetyl-2-methylnaphthalene 1-(α-Bromo)acetyl-2-methylnaphthalene (5.7 g) was synthesized from 2-methyl-1-acetylnaphthalene (4 g) in an analogous manner to that described in Example 5a.

$^1$H NMR (CDCl$_3$, δ): 2.45 (3H, s); 4.45 (2H, s); 7.35-7.9 (6H, m)

b. Synthesis of 1-(α-acetoxy)acetyl-2-methylnaphthalene 1-(α-Bromo)acetyl-2-methylnaphthalene (5.7 g) and sodium acetate (2.5 g) were stirred at 110° C. in anhydrous dimethylformamide (20 ml) for 5 hours. The mixture was cooled, added to water and extracted twice with ethyl acetate. The combined organic extracts were washed twice with water, brine, dried with sodium sulphate, filtered and evaporated in vacuo. The title compound was obtained as an oil (3.7 g) following silica gel column chromatography of the residue in dichloromethane.

$^1$H NMR (CDCl$_3$, δ): 2.2 (3H, s); 2.4 (3H, s); 5.0 (2H, s); 7.3-7.9 (6H, m)

c. Synthesis of 1-(α-hydroxy)acetyl-2-methylnaphthalene (E)

A mixture of 1-(α-acetoxy)acetyl-2-methylnaphthalene (3.7 g), IMS (60 ml) and hydrochloric acid (2M; 25 ml) was boiled under reflux for 3 hours. The mixture was cooled, evaporated and partitioned between ethyl acetate and brine. The organic layer was separated, washed with brine, dried with sodium sulphate, filtered and evaporated in vacuo. The title compound was obtained as an oil (2.8 g) following silica gel column chromatography of the residue in dichloromethane.

$^1$H NMR (CDCl$_3$, δ): 2.4 (3H, s); 3.45 (1H, t); 4.65 (2H, d); 7.35-7.9 (6H, m)

d. Synthesis of 2-amino-4-(2'-methylnaphth-1-yl)oxazole 1-(α-Hydroxy)acetyl-2-methylnaphthalene (E)(2.8 g) and cyanamide (0.71 g) were boiled to reflux in anhydrous ethanol (10 ml) for 16 hours. The ethanol was distilled off and the residue stirred at 105° C. for a further 24 hours. The mixture was cooled, triturated in chloroform (15 ml) and filtered. The title compound (6) was obtained as a pale yellow solid (0.36 g; melts slowly from 130° C.) following column chromatography of the chloroform solution on silica gel in 50% ethyl acetate in petroleum ether.

¹H NMR (CDCl₃, δ): 2.45 (3H, s); 4.75 (2H, broad s); 6.8 (1H, s): 7.35-7.9 (6H, s) Mass spectrum (m/z): 225 (M+H)⁺ Microanalysis: C expected 74.98 found 74.79; H expected 5.39 found 5.63; N expected 12.49 found 11.46

EXAMPLE 7

Synthesis of 2-amino-4-isopropyl-5-(naphth-1-yl)oxazole (7)

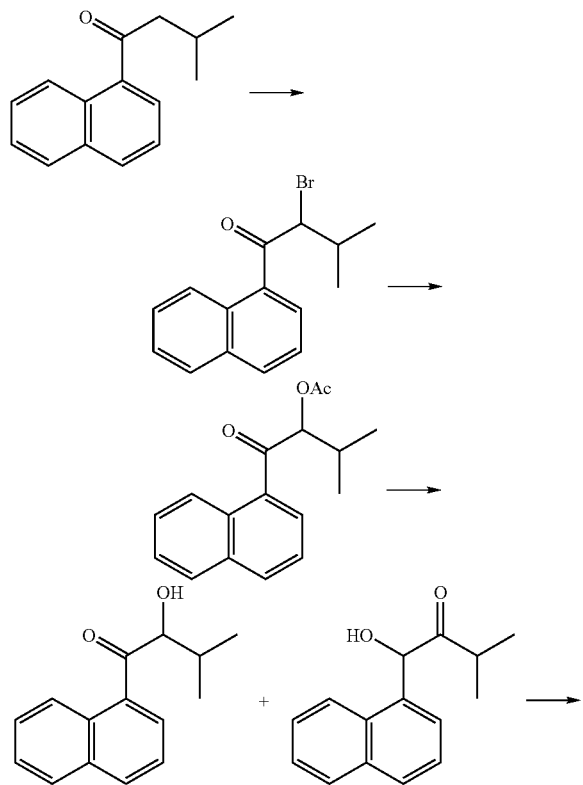

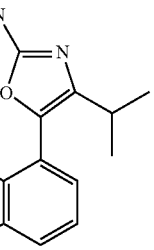

(7)

a. Synthesis of 2-acetoxy-3-methyl-1-(naphth-1-yl)butan-1-one

To a solution of 3-methyl-1-(naphth-1-yl)butan-1-one (20 g) in anhydrous tetrahydrofuran (150 ml) was added phenyltrimethylammonium tribromide (35.7 g). The resulting mixture was stirred overnight at ambient temperature then partitioned between petroleum ether and water. The organic layer was separated, washed with water, brine, dried with sodium sulphate, filtered and evaporated in vacuo to yield crude 2-bromo-3-methyl-1-(naphth-1-yl)butan-1-one. Sodium acetate (7.7 g) and anhydrous dimethylformamide (40 ml) were added and the resulting mixture was stirred at 100° C. for 6 hours. After cooling, the mixture was partitioned between ethyl acetate and water. The aqueous layer was back-extracted once with ethyl acetate. The combined organic layers were washed with water, brine, dried with sodium sulphate, filtered and evaporated in vacuo. The title compound (8.4 g) was obtained following silica gel column chromatography of the residue in 50% dichloromethane in petroleum ether.

¹H NMR (CDCl₃, δ): 1.0 (6H, dd); 2.25 (3H, s); 2.25 (1H, m); 5.8 (1H, d); 7.6 (3H, m); 7.95 (3H, m); 8.4 (1H, d)

b. Synthesis of 2-amino-4-isopropyl-5-(naphth-1-yl)oxazole

A mixture of 2-acetoxy-3-methyl-1-(naphth-1-yl)butan-1-one (8.4 g), IMS (200 ml) and hydrochloric acid (1M; 100 ml) were boiled under reflux for 4 hours. The mixture was cooled, evaporated in vacuo and partitioned between dichloromethane and brine. The organic layer was separated, dried with sodium sulphate, filtered and evaporated in vacuo to afford a mixture of crude 2-hydroxy-3-methyl-1-naphthalen-1-yl-butan-1-one and 1-hydroxy-3-methyl-1-naphthalen-1-yl-butan-2-one (F) (7.4 g). Cyanamide (1.3 g) and anhydrous ethanol (50 ml) were added and the resulting mixture was boiled under reflux for 96 hours. After cooling the volatiles were removed in vacuo and the residue heated at 115° C. for a further 48 hours. The mixture was cooled, triturated with chloroform (80 ml) and filtered. The filtrate was washed with water, dried with sodium sulphate, filtered and evaporated in vacuo. The title compound (7) was obtained (0.26 g; m.p. 127-129° C.) following silica gel column chromatography of the residue in 33% ethyl acetate in petroleum ether and re-crystallisation from dichloromethane/petroleum ether.

¹H NMR (CDCl₃, δ): 1.25 (6H, d); 2.85 (1H, septet); 5.2 (2H, broad s); 7.5 (4H, m); 7.9 (2H, m); 8.05 (1H, m) Mass spectrum (m/z): 253 (M+H)⁺ Microanalysis: C expected 76.16 found 76.22; H expected 6.39 found 6.37; N expected 11.10 found 11.03

EXAMPLE 8

Synthesis of 2-dimethylamino-4-(naphth-1-yl)oxazole (8)

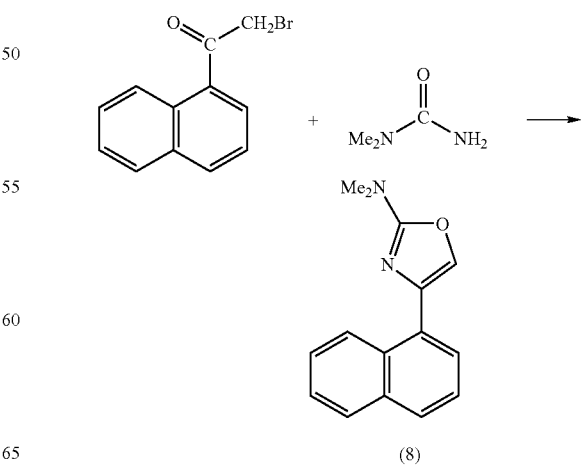

(8)

1-(α-Bromoacetyl)naphthalene (5 g) and 1,1-dimethylurea (6 g) were stirred in anhydrous dimethylformamide (20 ml) at 105° C. overnight. The mixture was cooled, added to ethyl acetate, washed with sodium bicarbonate solution, water, brine, dried with sodium sulphate, filtered and evaporated in vacuo. The title compound was obtained (0.60 g; m.p. 30-32° C.) following silica gel column chromatography of the residue in dichloromethane.

$^1$H NMR (CDCl$_3$, δ): 3.15 (6H, s); 7.5 (4H, m); 7.8 (3H, m); 8.45 (1H, m) Mass spectrum (m/z): 239 (M+H)$^+$ Microanalysis: C expected 75.61 found 75.54; H expected 5.92 found 5.99; N expected 11.76 found 11.56

EXAMPLE 9

Synthesis of 2-acetylamino-4-(naphth-1-yl)oxazole (9)

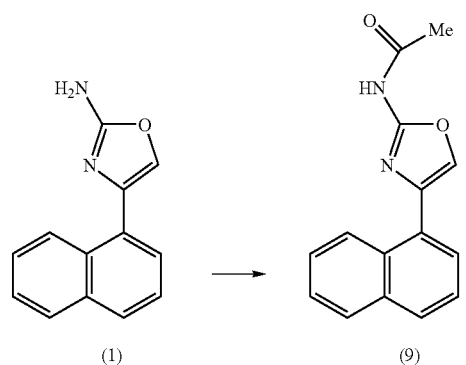

To a cooled (ice/salt bath) mixture of 2-amino-4-(naphth-1-yl)oxazole (1)(0.5 g) and triethylamine (0.8 ml) in anhydrous dichloromethane (5 ml) was added dropwise acetyl chloride (0.2 ml) over a minute. The resulting mixture was warmed to room temperature and left overnight. Further acetyl chloride (0.1 ml) was added and the mixture left for a further hour. Dichloromethane (40 ml) and few drops of methanol were added. The mixture was washed twice with brine, dried with sodium sulphate, filtered and evaporated in vacuo. The title compound (9) (0.35 g; m.p. 188-190° C.) was obtained following silica gel column chromatography of the residue in 2% methanol in chloroform.

$^1$H NMR (CDCl$_3$, δ): 2.4 (3H, broad s); 7.35 (1H, s); 7.55 (3H, m); 7.75 (1H, d); 7.9 (2H, t); 8.3 (1H, m) Mass spectrum (m/z): 275 (M+Na)$^+$ Microanalysis: (for 0.1 moles of water) C expected 70.91 found 70.93; H expected 4.84 found 4.86; N expected 11.03 found 10.99

EXAMPLE 10A

Synthesis of 4-(2-ethoxy-naphthalen-1-yl)-oxazol-2-ylamine (10)

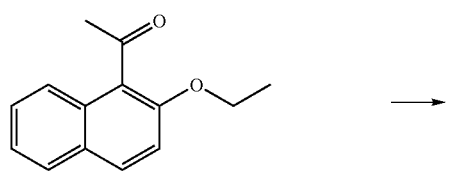

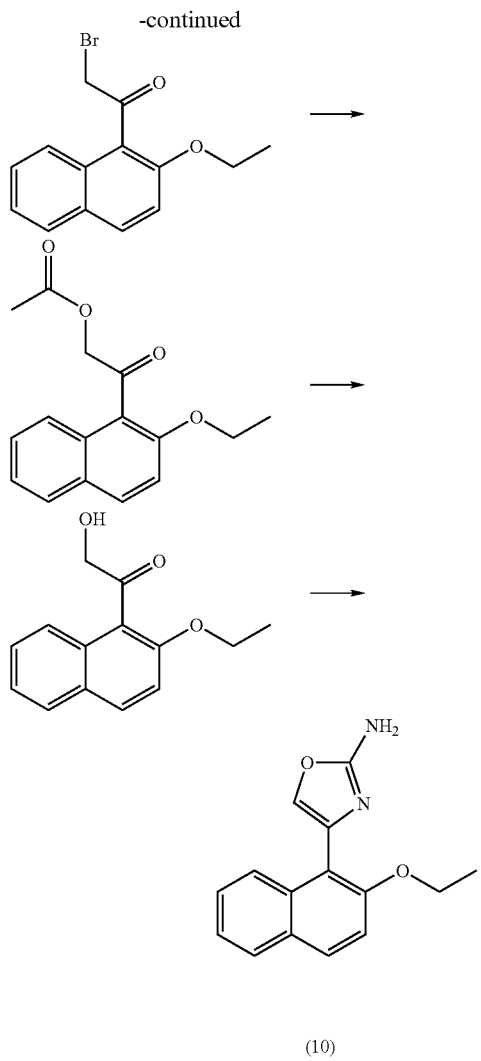

a. 2-bromo-1-(2-ethoxy-naphthalen-1-yl)-ethanone

To a solution of 1-(2-ethoxy-naphthalen-1-yl)-ethanone (26 g) in tetrahydrofuran (200 mL) at 0° C. was added phenyl trimethylammonium tribromide (50 g). The mixture was stirred at 0° C. for 10 minutes and then at room temperature for 4.5 hours. The mixture was washed with water (200 mL) and the aqueous phase was extracted with diethyl ether. The combined organics were washed with water (200 mL), dried over magnesium sulfate, filtered and the solvent removed under reduced pressure to afford a dark green sticky solid. The sticky solid was triturated with diethyl ether (100 mL) and filtered to give 2,2-dibromo-1-(2-ethoxy-naphthalen-1-yl)-ethanone (12.6 g, 35%) as an off-white solid. The filtrate was evaporated to a dark green oil and purified by column chromatography, elution with 40% to 60% dichloromethane in cyclohexane, affording 2-bromo-1-(2-ethoxy-naphthalen-1-yl)-ethanone (15.8 g, 44%) as an off-white solid. $^1$H NMR (CDCl$_3$): 1.45 (3H, m), 4.2 (2H, m), 4.5 (2H, m), 7.2 (1H, m), 7.4 (1H, m), 7.5 (1H, m), 7.8 (2H, m), 7.9 (1H, m).

b. Acetic acid 2-(2-ethoxy-naphthalen-1-yl)-2-oxo-ethyl ester

A mixture of 2-bromo-1-(2-ethoxy-naphthalen-1-yl)-ethanone (7.0 g), sodium acetate (2.0 g) and N,N-dimethylformamide (80 mL) was heated at 80° C. for 1.5 hours. After cooling to room temperature the N,N-dimethylformamide was removed under reduced pressure and the resulting residue was partitioned between dichloromethane (60 mL) and water (60 mL). The organic phase was washed with water (60 mL), brine (60 mL), dried over magnesium sulfate, filtered and the solvent removed under reduced pressure to afford acetic acid 2-(2-ethoxy-naphthalen-1-yl)-2-oxo-ethyl ester (6.1 g, 94%) as dark red oil. $^1$H NMR (CDCl$_3$): 1.45 (3H, t, J=7.0 Hz), 2.2 (3H, s), 4.2 (2H, q, J=7.0 Hz), 5.15 (2H, s), 7.2 (1H, d, J=9.4 Hz), 7.35 (1H, m), 7.45 (1H, m), 7.75 (1H, d, J=8.1 Hz), 7.85 (2H, m).

c. 1-(2-ethoxy-naphthalen-1-yl)-2-hydroxy-ethanone

A solution of acetic acid 2-(2-ethoxy-naphthalen-1-yl)-2-oxo-ethyl ester (6.1 g), industrial methylated spirits (40 mL) and 1M hydrochloric acid (30 mL) was heated at reflux for 2 hours. After cooling to room temperature, the solvent was removed under reduced pressure to afford a brown oil. Purification by column chromatography, eluting with 30% to 40% ethyl acetate in cyclohexane, afforded 1-(2-ethoxy-naphthalen-1-yl)-2-hydroxy-ethanone (3.7 g, 71%) as an orange solid. $^1$H NMR (CDCl$_3$): 1.4 (3H, t, J=7.0 Hz), 3.5 (1H, t, J=5.1 Hz), 4.2 (2H, q, J=7.0 Hz), 4.75 (2H, d, J=5.1 Hz), 7.25 (1H, d, J=9.0 Hz), 7.35 (1H, m), 7.5 (1H, m), 7.75 (1H, d, J=8.1 Hz), 7.85 (1H, d, J=7.8 Hz), 7.9 (1H, d, J=9.0 Hz).

d. 4-(2-ethoxy-naphthalen-1-yl)-oxazol-2-ylamine

A solution of 1-(2-ethoxy-naphthalen-1-yl)-2-hydroxy-ethanone (670 mg), cyanamide (2.0 g) and N,N-dimethylformamide (16 mL) was split equally between 8 microwave vials. These vials were heated at 250° C. and treated with microwave irradiation for 600 seconds. The contents from each of the vials were combined in a round-bottomed flask and the N,N-dimethylformamide was removed under reduced pressure. The residue was partitioned between ethyl acetate (80 mL) and water (80 mL). The organic phase was washed with water (2×80 mL), dried over magnesium sulfate, filtered and the solvent removed under reduced pressure to afford a dark brown gum. Purification by column chromatography afforded 4-(2-ethoxy-naphthalen-1-yl)-oxazol-2-ylamine (1.15 g, 28%) as a brown crystalline solid. $^1$H NMR (DMSO-D6): 1.3 (3H, t, J=7.0 Hz), 4.2 (2H, q, J=7.0 Hz), 6.65 (2H, br s), 6.9 (1H, s), 7.35 (1H, m), 7.45 (2H, m), 7.85 (2H, m), 8.0 (1H, d, J=8.6 Hz). Mass Spectrum (m/z): 255 (M+H)$^+$.

EXAMPLE 10B

Synthesis of 4-(4-methoxy-naphthalen-1-yl)-oxazol-2-ylamine (11)

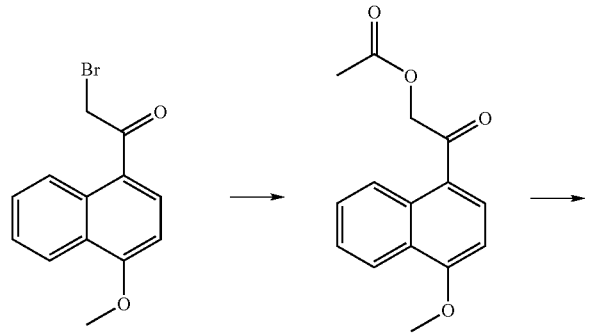

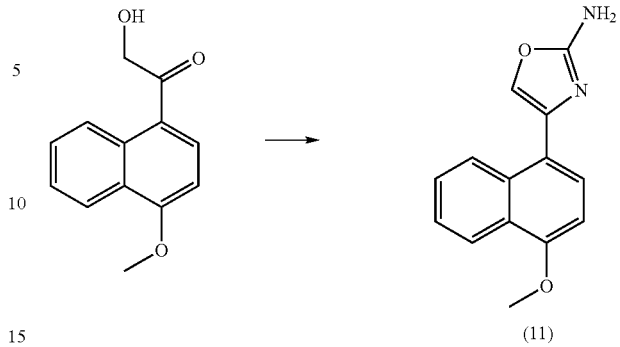

a. Acetic acid 2-(4-methoxy-naphthalen-1-yl)-2-oxo-ethyl ester was synthesised from 2-bromo-1-(4-methoxy-naphthalen-1-yl)-ethanone according to the method in Example 10A (b) (2.0 g, 92%) as a yellow solid.

b. 2-hydroxy-1-(4-methoxy-naphthalen-1-yl)-ethanone (830 mg, 52%) was synthesised from acetic acid 2-(4-methoxy-naphthalen-1-yl)-2-oxo-ethyl ester according to the method in Example 10A(c) as an orange gum; $^1$H NMR (CDCl$_3$): 3.8 (1H, t, J=4.7 Hz), 4.05 (3H, s), 4.85 (2H, d, J=4.7 Hz), 6.8 (1H, d, J=8.6 Hz), 7.55 (1H, ddd, J=8.4, 7.0, 1.1 Hz), 7.65 (1H, ddd, J=8.6, 6.9, 1.4 Hz), 7.9 (1H, d, J=8.4 Hz), 8.3 (1H, d, J=8.4 Hz), 9.1 (1H, d, J=8.6 Hz)

c. 4-(4-methoxy-naphthalen-1-yl)-oxazol-2-ylamine (11) was synthesised from 2-hydroxy-1-(4-methoxy-naphthalen-1-yl)-ethanone according to the method in Example 10A(d) as a brown crystalline solid (207 mg, 67%); $^1$H NMR (CDCl$_3$): 4.0 (3H, s), 4.8 (2H, br s), 6.8 (1H, d, J=7.9 Hz), 6.95 (1H, s) 7.45-7.55 (3H, m), 8.2 (1H, m), 8.3 (1H, m), Mass Spectrum (m/z): 241 (M+H)$^+$

EXAMPLE 10C

Synthesis of 4-(2-benzyloxy-naphthalen-1-yl)-oxazol-2-ylamine (12)

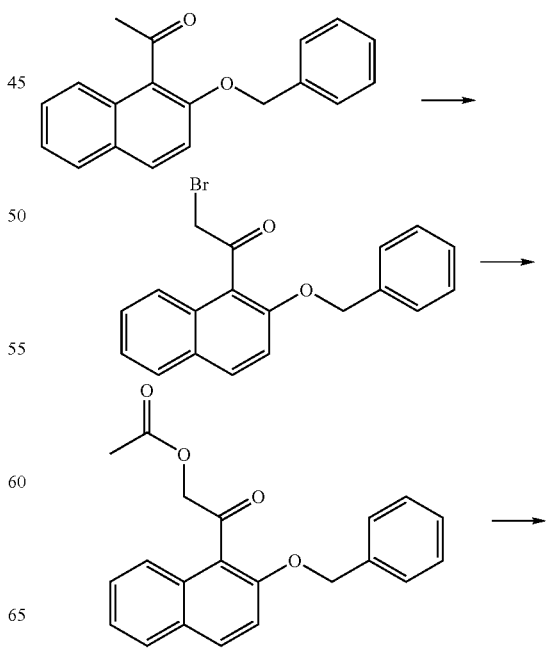

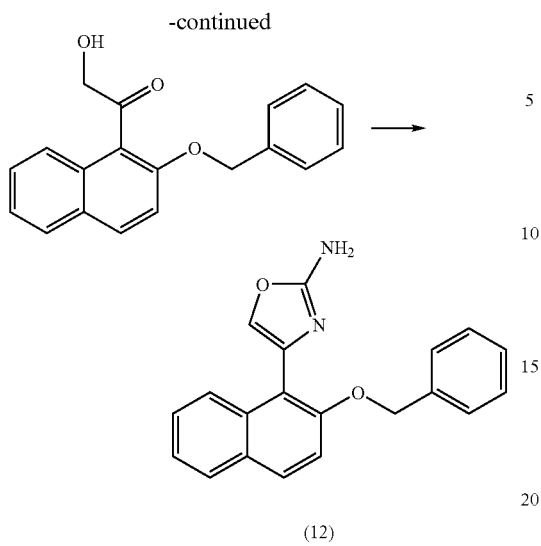

(12)

a. 1-(2-benzyloxy-naphthalen-1-yl)-2-bromo-ethanone was sythesised from 1-(2-benzyloxy-naphthalen-1-yl)-ethanone according to the method in Example 10A(a) (10.2 g, 74%) as a white solid, $^1$H NMR (DMSO-D6): 4.7 (2H, s), 5.35 (2H, s), 7.3-7.6 (9H, m), 7.9 (1H, d, J=8.1 Hz), 8.05 (1H, d, J=9.0 Hz).

b. Acetic acid 2-(2-benzyloxy-naphthalen-1-yl)-2-oxo-ethyl ester was synthesised from 1-(2-benzyloxy-naphthalen-1-yl)-2-bromo-ethanone according to method in Example 10A(b) (13.2 g, 100%) as a brown oil; $^1$H NMR (DMSO-D6): 2.1 (3H, s), 5.05 (2H, s), 5.3 (2H, s), 7.3-7.5 (7H, m), 7.6 (1H, d, J=9.2 Hz), 7.7 (1H, d, J=8.6 Hz), 7.9 (1H, d, J=7.9 Hz), 8.05 (1H, d, J=9.2 Hz).

c. 1-(2-benzyloxy-naphthalen-1-yl)-2-hydroxy-ethanone was synthesised from acetic acid 2-(2-benzyloxy-naphthalen-1-yl)-2-oxo-ethyl ester according to the method in Example 10A(c) (9.3 g, 81%) as an orange oil; $^1$H NMR (DMSO-D6): 4.45 (2H, d, J=6.0 Hz), 5.3 (2H, s), 5.4 (1H, t, J=6.0 Hz), 7.25-7.55 (9H, m), 7.85 (1H, d, J=8.3 Hz), 8.0 (1H, d, J=9.0 Hz).

d. 4-(2-benzyloxy-naphthalen-1-yl)-oxazol-2-ylamine was syntheised from 1-(2-benzyloxy-naphthalen-1-yl)-2-hydroxy-ethanone according to the method in Example 10A(d) as a brown solid (1.2 g, 12%); $^1$H NMR (DMSO-D6): 5.25 (2H, s), 6.7 (2H, br s), 6.9 (1H, s), 7.25-7.45 (7H, m), 7.5 (1H, d, J=9.0 Hz), 7.8 (1H, d, J=7.7 Hz), 7.9 (1H, d =9.0 Hz), 8.0 (1H, d, J=9.2 Hz); Mass Spectrum (m/z): 317 (M+H)$^+$.

EXAMPLE 10D

Synthesis of 4-(7-bromo-naphthalen-1-yl)-oxazol-2-ylamine (5) (see also Example 5)

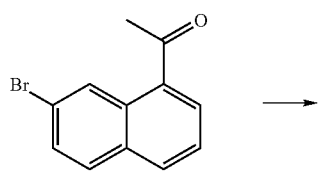

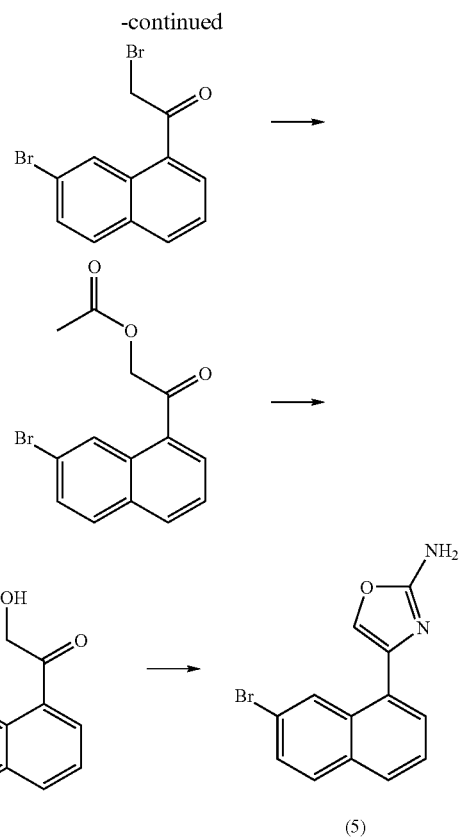

(5)

a. 2-bromo-1-(7-bromo-naphthalen-1-yl)-ethanone was synthesised from 1-(7-bromo-naphthalen-1-yl)-ethanone according to the method in Example 10A(a)(29.7 g, 96%) as an off-white solid; $^1$H NMR (CDCl$_3$): 4.55 (2H, s), 7.5 (1H, m), 7.6 (1H, m), 7.75 (1H, d, J=8.8 Hz), 7.95-8.0 (2H, m), 8.9 (1H, d, J=1.3 Hz).

b. Acetic acid 2-(7-bromo-naphthalen-1-yl)-2-oxo-ethyl ester was synthesised from 2-bromo-1-(7-bromo-naphthalen-1-yl)-ethanone according to the method in Example 10A(b) (26 g, 100%) as a fawn solid; $^1$H NMR (CDCl$_3$): 2.3 (3H, s), 5.3 (2H, s), 7.5 (1H, d, J=8.1, 7.2 Hz), 7.6 (1H, m), 7.7 (1H, d, J=8.5 Hz), 7.9 (1H, dd, J=7.2, 1.1 Hz), 8.0 (1H, d, J=8.3 Hz), 8.9 (1H, m).

c. 1-(7-bromo-naphthalen-1-yl)-2-hydroxy-ethanone was synthesised from acetic acid 2-(7-bromo-naphthalen-1-yl)-2-oxo-ethyl ester according to the method in Example 10A(c) (17 q, 79%) as a yellow solid; $^1$H NMR (CDCl$_3$): 4.85 (2H, s), 7.5 (1H, dd, J=8.2, 7.4 Hz), 7.65 (1H, dd, J=8.8, 2.0 Hz), 7.7 (1H, d, J=8.8 Hz), 7.9 (1H, dd, J=7.2, 1.1 Hz), 8.0 (1H, d, J=8.1 Hz), 9.15 (1H, d, J=2.0 Hz).

d. 4-(7-bromo-naphthalen-1-yl)-oxazol-2-ylamine was synthesized from 1-(7-bromo-naphthalen-1-yl)-2-hydroxy-ethanone according to the method in Example 10A(d) as a fawn solid (6.1 g, 33%); $^1$H NMR (DMSO-D6): 6.95 (2H, br s), 7.2 (1H, s), 7.55 (1H, dd, J=8.0, 7.4 Hz), 7.6-7.7 (2H, m), 7.85 (1H, d, J=8.1 Hz), 7.9 (1H, d, J=7.9 Hz), 8.4 (1H, d, J=1.8 Hz); Mass Spectrum (m/z): 289/291 (M+H)$^+$.

EXAMPLE 10E

Synthesis of 4-(3-methyl-benzo[b]thiophen-2-yl)-oxazol-2-ylamine (13)

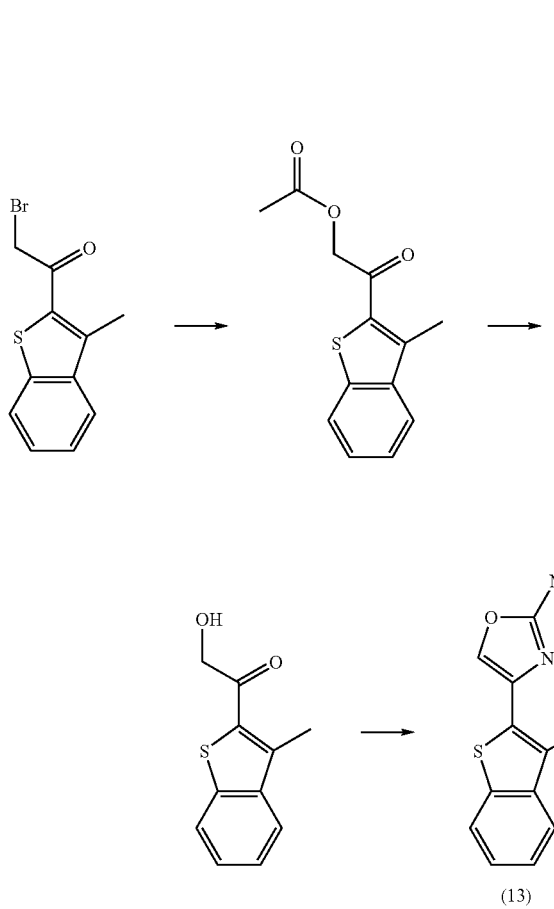

(13)

a. Acetic acid 2-(3-methyl-benzo[b]thiophen-2-yl)-2-oxo-ethyl ester was synthesised from 2-bromo-1-(3-methyl-benzo[b]thiophen-2-yl)-ethanone according to the method in Example 10A(b) (4.1 g, 90%) as a yellow solid; $^1$H NMR (DMSO-D6): 2.15 (3H, s), 2.7 (3H, s), 5.3 (2H, s), 7.45-7.55 (2H, m), 7.95-8.00 (2H, m).

b. 2-hydroxy-1-(3-methyl-benzo[b]thiophen-2-yl)-ethanone was syntheised from acetic acid 2-(3-methyl-benzo[b]thiophen-2-yl)-2-oxo-ethyl ester according to the method in Example 10A(c) (2.1 g, 65%) as a brown solid; $^1$H NMR (DMSO-D6): 2.65 (3H, s), 4.65 (2H, d, J=5.9 Hz), 5.3 (1H, t, J=5.9 Hz), 7.45-7.55 (2H, m), 7.95-8.00 (2H, m).

c. 4-(3-methyl-benzo[b]thiophen-2-yl)-oxazol-2-ylamine was synthesised from 2-hydroxy-1-(3-methyl-benzo[b]thiophen-2-yl)-ethanone according to the method in Example 10A(d) as an orange/brown solid (308 mg, 28%); $^1$H NMR (DMSO-D6): 2.4 (3H, s), 7.0 (2H, br s), 7.05 (1H, s), 7.3 (1H, m), 7.35 (1H, m), 7.7 (1H, m), 7.85 (1H, m), Mass Spectrum (m/z): 231 (M+H)$^+$.

EXAMPLE 10F

Synthesis of 4-(2-methyl-naphthalen-1-yl)-oxazol-2-ylamine (6) (see also example 6)

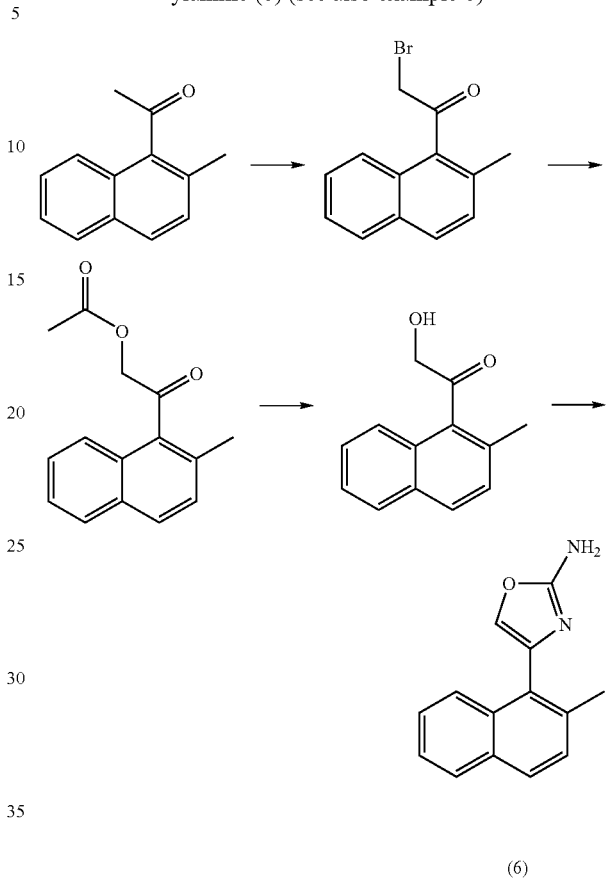

(6)

a. 2-bromo-1-(2-methyl-naphthalen-1-yl)-ethanone was synthesised from 1-(2-methyl-naphthalen-1-yl)-ethanone according to the method in Example 10A(a) (8.1 g, 94%) as a brown oil; $^1$H NMR (DMSO-D6): 2.35 (3H, s), 4.85 (2H, s), 7.4 (1H, d, J=8.6 Hz), 7.45-7.55 (3H, m), 7.90-7.95 (2H, m).

b. Acetic acid 2-(2-methyl-naphthalen-1-yl)-2-oxo-ethyl ester was synthesised from 2-bromo-1-(2-methyl-naphthalen-1-yl)-ethanone according to the method in Example 10A(b) (6.7 g, 93%) as an orange oil; $^1$H NMR (DMSO-D6): 2.15 (3H, s), 2.35 (3H, s), 5.15 (2H, s), 7.4 (1H, d, J=8.3 Hz), 7.45-7.55 (2H, m), 7.7 (1H, m), 7.9 (2H, m).

c. 2-hydroxy-1-(2-methyl-naphthalen-1-yl)-ethanone was synthesised from acetic acid 2-(2-methyl-naphthalen-1-yl)-2-oxo-ethyl ester according to the method in Example 10A(c) (5.2 g, 96%) as an orange oil; $^1$H NMR (DMSO-D6): 2.3 (3H, s), 4.45 (2H, s), 7.35 (1H, d, J=8.3 Hz), 7.45-7.50 (3H, m), 7.85-7.90 (2H, m).

d. 4-(2-methyl-naphthalen-1-yl)-oxazol-2-ylamine was synthesised from 2-hydroxy-1-(2-methyl-naphthalen-1-yl)-ethanone according to the method in Example 10A(d) as an orange solid (1.1 g, 20%); $^1$H NMR (DMSO-D6): 2.4 (3H, s), 6.7 (2H, br s), 6.8 (1H, s), 7.4-7.5 (3H, m), 7.75 (1H, m), 7.85 (2H, m); Mass Spectrum (m/z): 225 (M+H)$^+$.

EXAMPLE 10G

Synthesis of 4-(2,3-dihydro-benzo[1,4]dioxin-5-yl)-oxazol-2-ylamine (14)

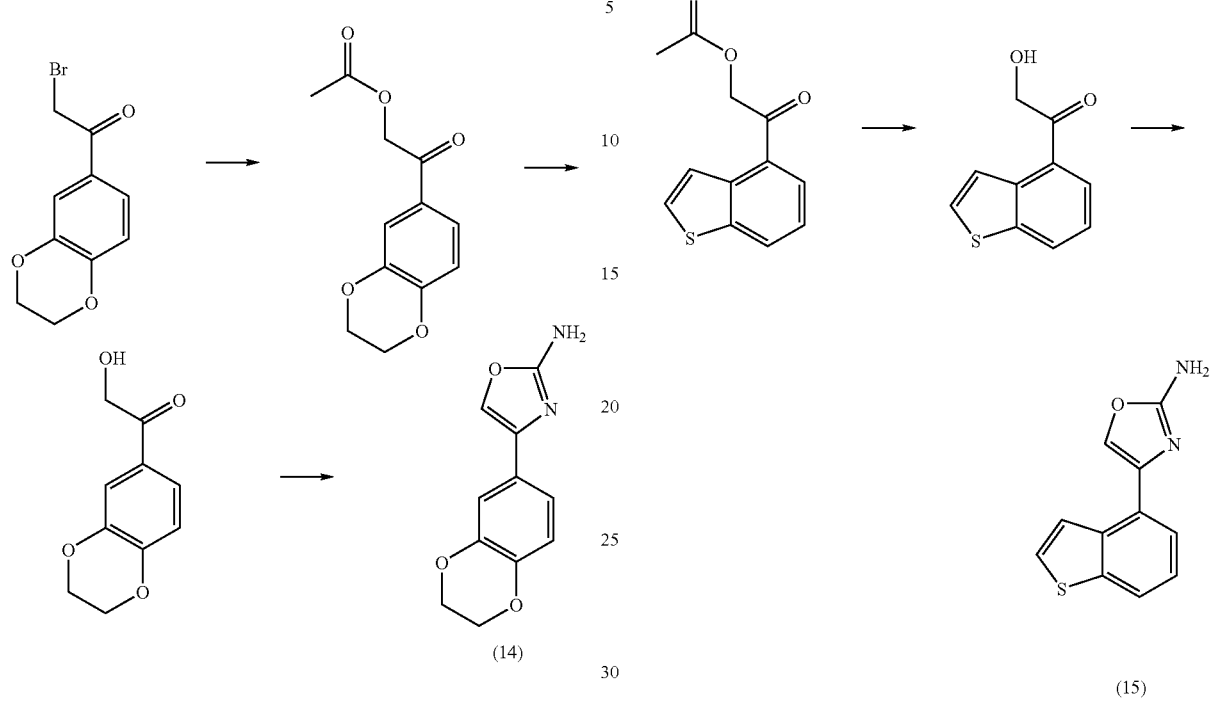

a. Acetic acid 2-(2,3-dihydro-benzo[1,4]dioxin-6-yl)-2-oxo-ethyl ester was synthesised from 2-bromo-1-(2,3-dihydro-benzo[1,4]dioxin-6-yl)-ethanone according to the method in Example 10A(b)(1.6 g, 89%) as a yellow solid; $^1$H NMR (DMSO-D6): 2.45 (3H, s), 4.25-4.35 (4H, m), 5.3 (2H, s), 6.95 (1H, d, J=8.3 Hz), 7.40-7.45 (2H, m).

b. (2,3-dihydro-benzo[1,4-]dioxin-6-yl)-2-hydroxy-ethanone was synthesised from acetic acid 2-(2,3-dihydro-benzo[1,4]dioxin-6-yl)-2-oxo-ethyl ester according to the method in Example 10A(c) (1.2 g, 97%) as a yellow solid; $^1$H NMR (CDCl$_3$): 4.25-4.30 (4H, m), 4.65 (2H, d, J=5.9 Hz), 4.9 (1H, t, J=5.9 Hz), 6.9 (1H, d, J=8.3 Hz), 7.35-7.40 (2H, m).

c. 4-(2,3-dihydro-benzo[1,4]dioxin-6-yl)-oxazol-2-ylamine was synthesised from (2,3-dihydro-benzo[1,4]dioxin-6-yl)-2-hydroxy-ethanone according to the method in Example 10A(d) as a light brown solid (113 mg, 17%); $^1$H NMR (DMSO-D6): 4.2 (4H, s), 6.65 (2H, br s), 6.8 (1H, m), 6.9 (2H, m), 6.95 (1H, s); Mass Spectrum (m/z): 219 (M+H)$^+$.

EXAMPLE 10H

Synthesis of 4-benzo[b]thiophen-4-yl-oxazol-2-ylamine (15)

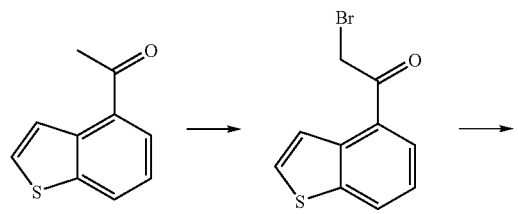

a. 1-benzo[b]thiophen-4-yl-2-bromo-ethanone was synthesised from 1-benzo[b]thiophen-4-yl-ethanone (available by the palladium coupling of 4-bromobenzo[b]thiophene with 1-vinyloxy-butane) according to the method in Example 10A(a) (6.8 g, 92%) as an orange oil; $^1$H NMR (CDCl$_3$): 4.6 (2H, s), 7.4 (1H, t, J=7.8 Hz), 7.65 (1H, d, J=5.7 Hz), 7.95 (1H, dd, J=7.8, 0.9 Hz), 8.1 (1H, dt, J=7.8, 0.9 Hz), 8.3 (1H, dd, J=5.7, 0.9 Hz).

b. Acetic acid 2-benzo[b]thiophen-4-yl-2-oxo-ethyl ester was synthesised from 1-benzo[b]thiophen-4-yl-2-bromo-ethanone according to the method in Example 10A(b) (5.8 g, 97%) as a yellow solid; $^1$H NMR (CDCl$_3$): 2.2 (3H, s), 5.4 (2H, s), 7.4 (1H, t, J=7.7 Hz), 7.65 (1H, d, J=5.5 Hz), 7.85 (1H, m), 8.0 (1H, m), 8.3 (1H, m).

c. 1-benzo[b]thiophen-4-yl-2-hydroxy-ethanone was synthesised from acetic acid 2-benzo[b]thiophen-4-yl-2-oxo-ethyl ester according to the method in Example 10A(c) (4.3 g, 91%) as a yellow gum; $^1$H NMR (DMSO-D6): 4.85 (2H, d, J=5.7 Hz), 5.1 (1H, t, J=5.7 Hz), 7.45 (1H, t, J=7.9 Hz), 7.95 (1H, d, J=5.5 Hz), 8.0 (1H, dd, J=7.6, 0.9 Hz), 8.15 (1H, dd, J=5.5, 0.9 Hz), 8.25 (1H, dt, J=8.0, 0.9 Hz).

d. 4-benzo[b]thiophen-4-yl-oxazol-2-ylamine was synthesised from 1-benzo[b]thiophen-4-yl-2-hydroxy-ethanone according to the method in Example 10A(d) as an orange powder (1.4 g, 30%); $^1$H NMR (DMSO-D6): 6.9 (2H, br s), 7.35 (2H, m), 7.5 (1H, m), 7.80-7.85 (3H, m); Mass Spectrum (m/z): 216 (M+H)$^+$.

EXAMPLE 10I

Synthesis of 4-naphthalen-2-yl-oxazol-2-ylamine (16)

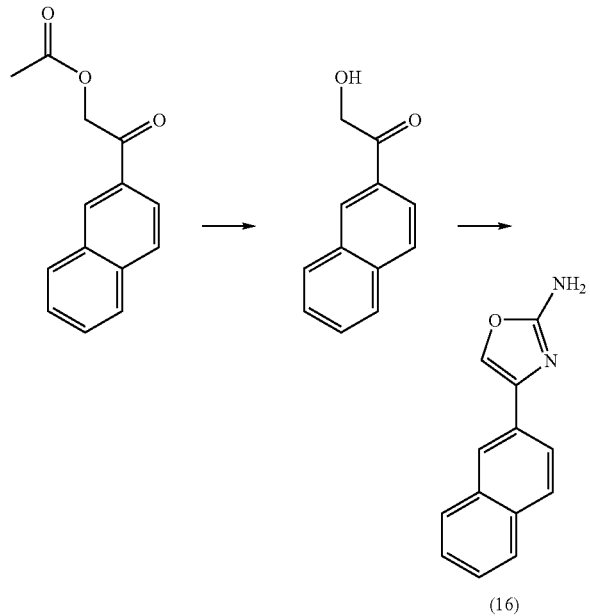

(16)

a. 2-hydroxy-1-naphthalen-2-yl-ethanone was synthesised from acetic acid 2-naphthalen-2-yl-2-oxo-ethyl ester according to the method in Example 10A(c) (1.2 g, 67%) as a pale yellow solid; $^1$H NMR (DMSO-D6): 4.95 (2H, d, J=5.9 Hz), 5.15 (1H, t, J=5.9 Hz), 7.6-7.7 (2H, m), 7.95-8.05 (3H, m), 8.1 (1H, d, J=8.0 Hz), 8.65 (1H, s).

b. 4-naphthalen-2-yl-oxazol-2-ylamine was synthesised from 2-hydroxy-1-naphthalen-2-yl-ethanone according to the method in Example 10A(d) (9 mg, 4%) as a brown solid; $^1$H NMR (DMSO-D6): 6.9 (2H, br s), 7.3 (1H, s), 7.4 (2H, m), 7.6 (1H, dd, J=8.6, 1.8 Hz), 7.85 (4H, m); Mass Spectrum (m/z): 211 (M+H)$^+$.

EXAMPLE 10J

Synthesis of 4-naphthalen-1-yl-oxazol-2-ylamine (1) (see also example 1)

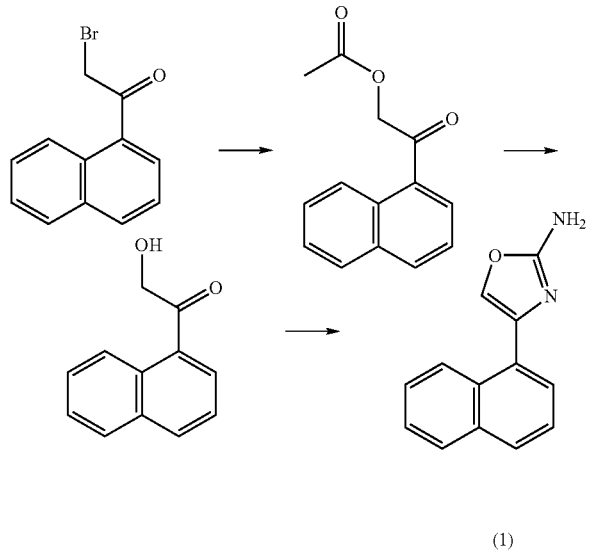

(1)

a. Acetic acid 2-naphthalen-1-yl-2-oxo-ethyl ester was synthesised from 2-bromo-1-naphthalen-1-yl-ethanone according to the method in Example 10A(b) (5.4 g, 72%) as a yellow oil; $^1$H NMR (CDCl$_3$): 2.2 (3H, s), 5.3 (2H, s), 7.45-7.60 (3H, m), 7.80-7.85 (2H, m), 8.0 (1H, m), 8.6 (1H, m).

b. 2-hydroxy-1-naphthalen-1-yl-ethanone was synthesised from acetic acid 2-naphthalen-1-yl-2-oxo-ethyl ester according to the method in Example 10A(c) (4.6 g, 100%) as an orange oil; $^1$H NMR (CDCl$_3$): 4.9 (2H, s), 7.45 (1H, dd, J=8.2, 7.4 Hz), 7.50-7.55 (1H, m), 7.6 (1H, ddd, J=8.6, 6.9, 1.4 Hz), 7.85-7.90 (2H, m), 8.05 (1H, d, J=8.3 Hz), 7.7 (1H, m).

c. 4-naphthalen-1-yl-oxazol-2-ylamine was synthesised from 2-hydroxy-1-naphthalen-1-yl-ethanone according to the method in Example 10A(d) as an orange powder (170 mg, 32%); $^1$H NMR (DMSO-D6): 6.85 (2H, br s), 7.2 (1H, s), 7.45-7.55 (3H, m), 7.6 (1H, m), 7.8 (1H, d, J=8.1 Hz), 7.90-7.95 (1H, m), 8.25-8.30 (1H, m); Mass Spectrum (m/z): 211 (M+H)$^+$.

EXAMPLE 10K

Synthesis of 4-(2-methoxy-naphthalen-1-yl)-oxazol-2-ylamine (17)

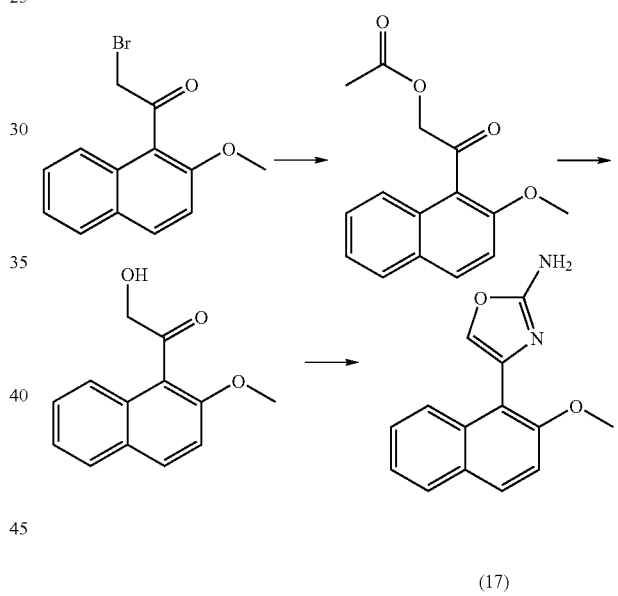

(17)

a. Acetic acid 2-(2-methoxy-naphthalen-1-yl)-2-oxo-ethyl ester was synthesised from 2-bromo-1-(2-methoxy-naphthalen-1-yl)-ethanone according to the method in Example 10A (b) (2.7 g, 35%) as a yellow solid; $^1$H NMR (CDCl$_3$): 2.1 (3H, s), 3.95 (3H, s) 5.1 (2H, s), 7.35-7.40 (1H, m), 7.45-7.5 (2H, m), 7.65 (1H, d, J=8.6 Hz), 7.9 (1H, d, J=8.1 Hz), 8.1 (1H, d, J=9.0 Hz).

b. 2-hydroxy-1-(2-methoxy-naphthalen-1-yl)-ethanone was synthesised from acetic acid 2-(2-methoxy-naphthalen-1-yl)-2-oxo-ethyl ester according to the method in Example 10A(c) (2.0 g, 92%) as a yellow solid; $^1$H NMR (DMSO-D6): 3.9 (3H, s), 4.45 (2H, d, J=6.1 Hz), 5.35 (1H, t, J=6.1 Hz), 7.35-7.50 (4H, m), 7.85 (1H, d, J=8.3 Hz), 8.0 (1H, d, J=9.2 Hz).

c. 4-(2-methoxy-naphthalen-1-yl)-oxazol-2-ylamine was synthesised from 2-hydroxy-1-(2-methoxy-naphthalen-1-yl)-ethanone according to the method in Example 10A(d) as a brown solid (400 mg, 37%); $^1$H NMR (DMSO-D6): 3.9 (3H, s), 6.65 (2H, br s), 6.85 (1H, s), 7.35 (1H, s), 7.4-7.5 (2H, m), 7.85 (1H, d, J=8.1 Hz), 7.95 (2H, m); Mass Spectrum (m/z): 241 (M+H)+.

EXAMPLE 10L

Synthesis of 4-(1-methoxy-naphthalen-2-yl)-oxazol-2-ylamine (18)

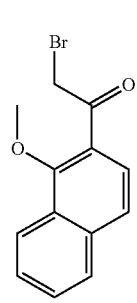
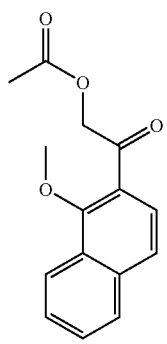

(18)

a. Acetic acid 2-(1-methoxy-naphthalen-2-yl)-2-oxo-ethyl ester was synthesised from 2-bromo-1-(2-methoxy-naphthalen-1-yl)-ethanone according to the method in Example 10A (b) (530 mg, 53%) as a yellow solid; $^1$H NMR (DMSO-D6): 2.1 (3H, s), 4.0 (3H, s), 5.35 (2H, s), 7.6-7.8 (4H, m), 8.0 (1H, m), 8.2 (1H, m).

b. 2-hydroxy-1-(1-methoxy-naphthalen-2-yl)-ethanone was synthesised from acetic acid 2-(1-methoxy-naphthalen-2-yl)-2-oxo-ethyl ester according to the method in Example 10A(c) (530 mg, 53%) as a yellow solid; $^1$H NMR (DMSO-D6): 3.95 (3H, s), 4.7 (2H, d, J=5.9 Hz), 5.1 (1H, t, J=5.9 Hz), 7.60-7.75 (4H, m), 7.95 (1H, m), 8.15 (1H, m).

c. 4-(1-methoxy-naphthalen-2-yl)-oxazol-2-ylamine was synthesised from 2-hydroxy-1-(1-methoxy-naphthalen-2-yl)-ethanone according to the method in Example 10A(d) as a brown solid (150 mg, 25%); $^1$H NMR (DMSO-D6): 3.8 (3H, s), 6.9 (2H, br s), 7.25 (1H, s), 7.45 (1H, m), 7.5 (1H, m), 7.6 (1H, d, J=8.8 Hz), 7.7 (1H, d, J=8.3 Hz), 7.85 (1H, d, J=7.5 Hz), 8.0 (1H, d, J=8.3 Hz); Mass Spectrum (m/z): 241 (M+H)+.

EXAMPLE 10M

Synthesis of 4-(5-bromo-naphthalen-1-yl)-oxazol-2-ylamine (19)

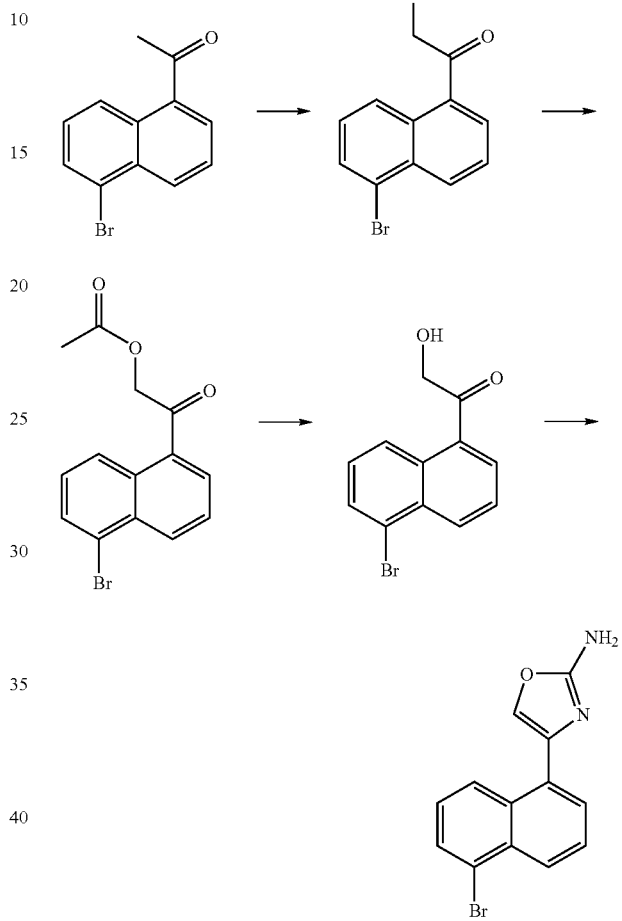

(19)

a. 2-bromo-1-(5-bromo-naphthalen-1-yl)-ethanone was synthesised from 1-(5-bromo-naphthalen-1-yl)-ethanone according to the method in Example 10A(a) (10.9 g, 100%) as an off-white solid; $^1$H NMR (CDCl$_3$): 4.5 (2H, s), 7.4 (1H, dd, J=8.9, 7.6 Hz), 7.6 (1H, dd, J=8.7, 7.1 Hz), 7.8-7.9 (2H, m), 8.5 (2H, m).

b. Acetic acid 2-(5-bromo-naphthalen-1-yl)-2-oxo-ethyl ester was synthesised from 2-bromo-1-(5-bromo-naphthalen-1-yl)-ethanone according to the method in Example 10A (b) (6.9 g, 72%) as a yellow solid; $^1$H NMR (CDCl$_3$): 2.2 (3H, s), 5.25 (2H, s), 7.4 (1H, m), 7.6 (1H, m), 7.85 (2H, d, J=7.2 Hz), 8.5 (2H, d, J=8.8 Hz).

c. 1-(5-bromo-naphthalen-1-yl)-2-hydroxy-ethanone was synthesised from acetic acid 2-(5-bromo-naphthalen-1-yl)-2-oxo-ethyl ester according to the method in Example 10A(c) (340 mg, 39%) as a white solid; $^1$H NMR (CDCl$_3$): 3.55 (1H, t, J=4.8 Hz), 4.85 (2H, d, J=4.8 Hz), 7.45 (1H, dd, J=8.6, 7.6 Hz), 7.6 (1H, dd, J=8.6, 7.2 Hz), 7.9 (2H, t, J=7.8 Hz), 8.55 (1H, d, J=8.6 Hz), 8.75 (1H, d, J=8.6 Hz).

d. 4-(5-bromo-naphthalen-1-yl)-oxazol-2-ylamine was synthesised from 1-(5-bromo-naphthalen-1-yl)-2-hydroxy-ethanone according to the method in Example 10A(d) as a pale brown solid (210 mg, 11%); $^1$H NMR (DMSO-D6): 6.95 (2H, br s), 7.25 (1H, s), 7.45 (1H, dd, J=8.6, 7.5 Hz), 7.65-7.70 (2H, m), 7.9 (1H, m), 8.0 (1H, m), 8.35 (1H, m); Mass Spectrum (m/z): 289/291 (M+H)$^+$.

EXAMPLE 11A

Synthesis of 4-(7-carbonitrile-naphthalen-1-yl)-oxazol-2-ylamine (20)

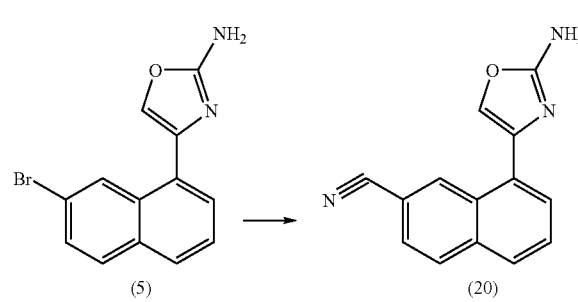

A mixture of 4-(7-bromo-naphthalen-1-yl)-oxazol-2-ylamine (5, 0.20 g), zinc cyanide (81 mg), palladium (0) tetrakis(triphenylphosphine) (57 mg) and N,N-dimethylformamide (3.5 mL) was treated with microwave irradiation for 5 minutes at 180° C. The reaction mixture was partitioned between ethyl acetate (40 mL) and water (40 mL). The organic phase was washed with water (40 mL), dried over magnesium sulfate, filtered and the solvent removed under reduced pressure to afford a bright yellow solid. Purification by column chromatography, eluting with 30% ethyl acetate in dichloromethane, afforded a bright yellow solid, which was recrystallised from industrial methylated spirits to afford 4-(7-carbonitrile-naphthalen-1-yl)-oxazol-2-ylamine (20) as a bright yellow solid (32 mg, 20%). $^1$H NMR (DMSO-D6): 7.05 (2H, br s), 7.4 (1H, s), 7.65-7.75 (2H, m), 7.8 (1H, dd, J=8.3, 1.5 Hz), 7.9 (1H, d, J=7.9 Hz), 8.1 (1H, d, J=8.6 Hz), 8.75 (1H, s). Mass Spectrum (m/z): 236 (M+H)$^+$.

EXAMPLE 11B

Synthesis of 4-(5-carbonitrile-naphthalen-1-yl)-oxazol-2-ylamine (21)

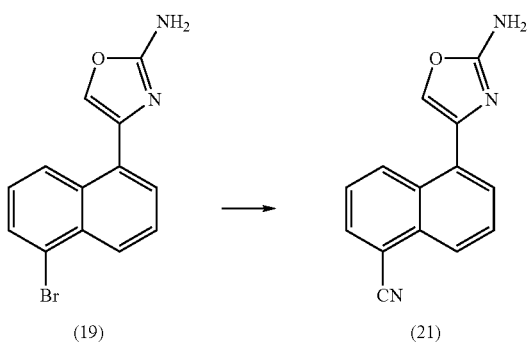

4-(5-carbonitrile-naphthalen-1-yl)-oxazol-2-ylamine (21) was prepared from 4-(5-bromo-naphthalen-1-yl)-oxazol-2-ylamine (19) according to the method of Example 11A as a brown solid (240 mg, 5%); $^1$H NMR (DMSO-D6): 7.35 (1H, s), 7.7 (1H, dd, J=8.8, 7.3 Hz), 7.80-7.85 (2H, m), 8.0 (1H, dd, J=6.6, 2.7 Hz), 8.2 (1H, dd, J=7.1, 1.0 Hz), 8.7 (1H, d, J=8.6 Hz); Mass Spectrum (m/z): 236 (M+H)$^+$.

EXAMPLE 12

Synthesis of 1-(2-amino-oxazol-4-yl)-naphthalen-2-ol (22)

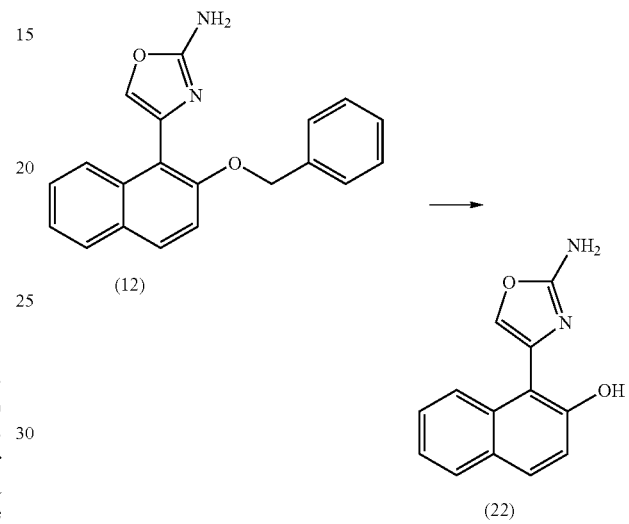

4-(2-Benzyloxy-naphthalen-1-yl)-oxazol-2-ylamine (12, 1.0 g) was dissolved in ethanol and then palladium, 10% on carbon (390 mg) was added. The mixture was stirred under 1 atmosphere of hydrogen for 48 hours. The mixture was filtered through a pad of hyflo and washed with industrial methylated spirits. The filtrate was concentrated under reduced pressure and the residue was purified by column chromatography to afford 1-(2-amino-oxazol-4-yl)-naphthalen-2-ol (22) (290 mg, 41%) as a glassy orange foam. $^1$H NMR (DMSO-D6): 6.6 (2H, br s), 6.85 (1H, s), 7.2 (1H, d, J=9.0 Hz), 7.25 (1H, m), 7.4 (1H, m), 7.75 (2H, m), 7.9 (1H, m), 9.9 (1H, br s). Mass Spectrum (m/z): 227 (M+H)$^+$.

EXAMPLE 13

Synthesis of [1-(2-amino-oxazol-4-yl)-naphthalen-2-yloxy]-acetic acid methyl ester (23)

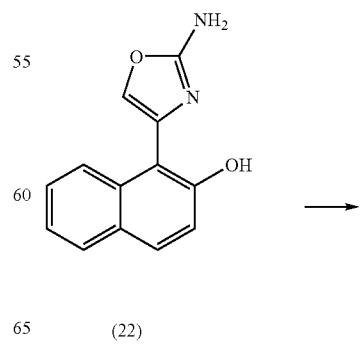

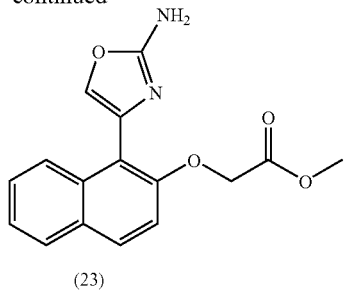

(23)

1-(2-Amino-oxazol-4-yl)-naphthalen-2-ol (22, 190 mg) was dissolved in N,N-dimethylformamide and then sodium hydride (34 mg) was added in one portion to give a dark orange solution. Methyl bromoacetate (88 μL) was then added and the mixture was stirred at room temperature for 18 hours.

The solvent was removed under reduced pressure and the residue was partitioned between ethyl acetate and water. The organic phase was dried over magnesium sulfate, filtered and the solvent removed under reduced pressure to afford an orange gum. The orange gum was triturated with diethyl ether and the solid filtered to afford [1-(2-amino-oxazol-4-yl)-naphthalen-2-yloxy]-acetic acid methyl ester (23) (164 mg, 65%) as a fawn solid. $^1$H NMR (DMSO-D6): 3.65 (3H, s), 4.95 (2H, s), 6.7 (2H, br s), 7.05 (1H, s), 7.35 (3H, m), 7.45 (1H, m), 7.85 (1H, m), 8.1 (1H, d, J=8.6 Hz). Mass Spectrum (m/z): 299 (M+H)$^+$.

EXAMPLE 14

Synthesis of 8-(2-amino-oxazol-4-yl)-naphthalene-2-carboxylic acid amide (24)

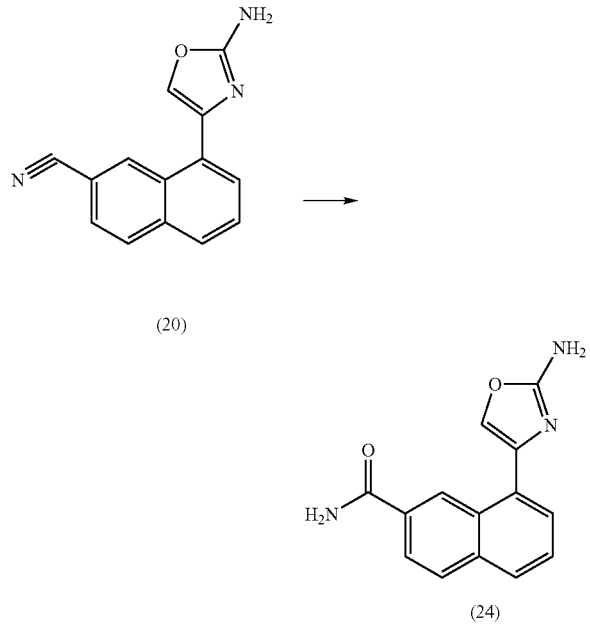

A mixture of 4-(7-carbonitrile-naphthalen-1-yl)-oxazol-2-ylamine (20, 50 mg), potassium hydroxide (70 mg) and industrial methylated spirits (5 mL) was heated at reflux for 6 hours. After cooling to room temperature the mixture was poured onto a mixture of ice (5 mL)/concentrated hydrochloric acid (1 mL). The solvent was removed under reduced pressure and the remaining aqueous residues were adjusted to pH 7 with solid sodium hydrogen carbonate. This solution was extracted with ethyl acetate (2×10 mL). The combined organics were washed with water (10 mL), dried over magnesium sulfate, filtered and the solvent removed under reduced pressure to afford a yellow solid. This solid was purified using preparative HPLC, eluting with 20% acetonitrile in water with a 5 mL/minute flow rate, to afford 8-(2-amino-oxazol-4-yl)-naphthalene-2-carboxylic acid amide (24) (10 mg, 19%) as a white solid. $^1$H NMR (DMSO-D6): 7.5 (1H, br s), 7.55 (1H, br s), 7.6-7.7 (3H, m), 7.85 (1H, br s), 7.9-8.0 (3H, m), 8.15 (1H, br s), 8.65 (1H, s). Mass Spectrum (m/z): 254 (M+H)$^+$.

EXAMPLE 15

Synthesis of N-[4-(2-methoxy-naphthalen-1-yl)-oxazol-2-yl]-acetamide (25)

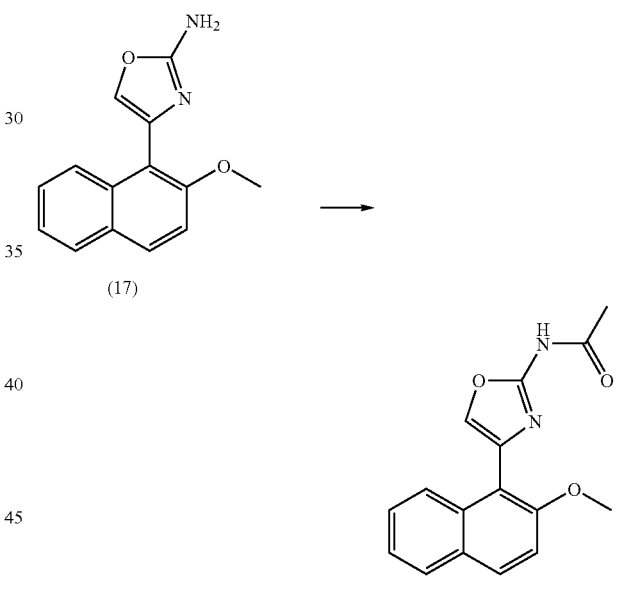

To a solution of 4-(2-methoxy-naphthalen-1-yl)-oxazol-2-ylamine (17, 450 mg), triethylamine (0.78 mL) and dichloromethane (5 mL) at 0° C. was added acetyl chloride (0.2 mL). The solution was allowed to warm to room temperature overnight and the reaction was quenched by the addition of a mixture of dichloromethane and methanol. The solution was washed with brine (×2), dried over magnesium sulfate, filtered and the solvent removed under reduced pressure. The residue was purified by column chromatography, eluting with 2% methanol in dichloromethane, to afford N-[4-(2-methoxy-naphthalen-1-yl)-oxazol-2-yl]-acetamide (25) (190 mg, 36%) as an off-white solid. $^1$H NMR (DMSO-D6): 2.1 (3H, br s), 3.9 (3H, s), 7.2 (1H, s), 7.35-7.40 (1H, m), 7.45-7.50 (1H, m), 7.55 (1H, d, J=9.2 Hz), 7.90-7.95 (2H, m), 8.05 (1H, d, J=9.2 Hz), 11.2 (1H, br s). Mass Spectrum (m/z): 283 (M+H)$^+$.

EXAMPLE 16A

Synthesis of 4-methyl-5-naphthalen-1-yl-oxazol-2-ylamine (3) (see also example 3)

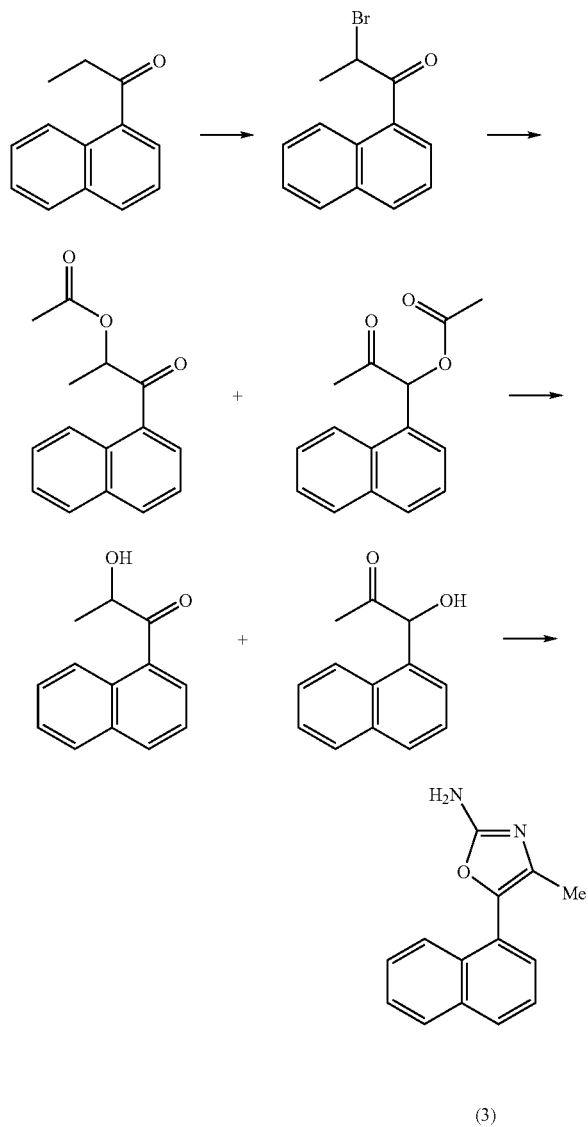

a. Synthesis of 2-bromo-1-naphthalen-1-yl-propan-1-one

To a solution of 1-naphthalen-1-yl-propan-1-one (37.8 g) in 1,2-dimethoxyethane (350 mL) at 0° C. was added phenyl trimethylammonium tribromide (83 g). The mixture was stirred at 0° C. for 10 minutes and then at room temperature for 24 hours. The mixture was washed with water (500 mL) and the aqueous phase was extracted with ethyl acetate (2×500 mL). The combined organics were washed with water (2×200 mL), brine (500 mL), dried over magnesium sulfate, filtered and the solvent removed under reduced pressure to afford an orange gum. The gum was triturated with diethyl ether and filtered to afford 2-bromo-1-naphthalen-1-yl-propan-1-one (39.8 g, 74%) as an orange solid, $^1$H NMR (CDCl$_3$): 1.95 (3H, d, J=6.6 Hz), 5.35 (1H, q, J=6.6 Hz), 7.45-7.60 (3H, m), 7.85-7.90 (2H, m), 8.0 (1H, d, J=8.1 Hz), 8.4 (1H, d, J=7.9 Hz).

b. Acetic acid 1-naphthalen-1-yl-2-oxo-propyl ester and Acetic acid 1-methyl-2-naphthalen-1-yl-2-oxo-ethyl ester (2:1 mixture)

A mixture of 2-bromo-1-naphthalen-1-yl-propan-1-one (20 g), sodium acetate (7.8 g) and N,N-dimethylformamide (300 mL) was heated at 80° C. for 18 hours. After cooling to room temperature the N,N-dimethylformamide was removed under reduced pressure and the resulting residue was partitioned between dichloromethane (300 mL) and water (300 mL). The organic phase was washed with water (300 mL), brine (300 mL), dried over magnesium sulfate, filtered and the solvent removed under reduced pressure to afford acetic acid 1-naphthalen-1-yl-2-oxo-propyl ester and acetic acid 1-methyl-2-naphthalen-1-yl-2-oxo-ethyl ester (2:1 mixture) (9.0 g, 49%) as a brown oil, $^1$H NMR (CDCl$_3$): 1.45 (3H, d, J=7.0 Hz), 2.05 (3H, s), 2.15 (3H, s), 2.2 (3H, s), 5.95 (1H, q, J=7.0 Hz), 6.65 (1H, s), 7.45-7.60 (7H, m), 7.85-7.90 (4H, m), 8.0 (1H, d, J=8.1 Hz), 8.1 (1H, d, J=8.3 Hz), 8.35 (1H, d, J=8.6 Hz).

c. 1-hydroxy-1-naphthalen-1-yl-propan-2-one and 2-hydroxy-1-naphthalen-1-yl-propan-1-one (4:1 mixture)

A solution of acetic acid 1-naphthalen-1-yl-2-oxo-propyl ester and acetic acid 1-methyl-2-naphthalen-1-yl-2-oxo-ethyl ester (2:1 mixture) (16.7 g), ethanol (300 mL) and 1M hydrochloric acid (150 mL) was heated at reflux for 4 hours. After cooling to room temperature, the ethanol was removed under reduced pressure and the aqueous phase was extracted with dichloromethane (200 mL). The organic phase was washed with water (2×150 mL), brine (2×150 mL) dried over magnesium sulfate, filtered and the solvent removed under reduced pressure to afford 1-hydroxy-1-naphthalen-1-yl-propan-2-one and 2-hydroxy-1-naphthalen-1-yl-propan-1-one (4:1 mixture) (12.0 g, 87%) as an orange oil, $^1$H NMR (DMSO-D6): 1.2 (3H, d, J=6.8 Hz), 2.0 (3H, s), 5.0 (1H, m), 5.35 (1H, d, J=6.5 Hz), 5.65 (1H, d, J=4.0 Hz), 6.15 (1H, d, J=4.0 Hz), 7.45-8.20 (10H, m).

d. 4-methyl-5-naphthalen-1-yl-oxazol-2-ylamine (3)

A solution of 1-hydroxy-1-naphthalen-1-yl-propan-2-one and 2-hydroxy-l-naphthalen-1-yl-propan-1-one (4:1 mixture) (2.0 g) cyanamide (1.3 g) and N,N-dimethylformamide (20 mL) was split equally between 10 microwave vials. These vials were heated at 200° C. and treated with microwave irradiation for 15 minutes. The contents from each of the vials were combined in a round-bottomed flask and the N,N-dimethylformamide was removed under reduced pressure. The residue was partitioned between ethyl acetate (100 mL) and water (100 mL). The organic phase was washed with water (2×100 mL), dried over magnesium sulfate, filtered and the solvent removed under reduced pressure to afford a dark brown gum. Purification by column chromatography afforded 4-methyl-5-naphthalen-1-yl-oxazol-2-ylamine (3) (602 mg, 43%) as a brown solid, $^1$H NMR (DMSO-D6): 1.95 (3H, s), 6.65 (2H, br s), 7.4-7.5 (4H, m), 7.85-7.95 (3H, s). Mass Spectrum (m/z): 225 (M+H)$^+$.

EXAMPLE 16B

Synthesis of 5-(2-methoxy-naphthalen-1-yl)-4-methyl-oxazol-2-ylamine (26)

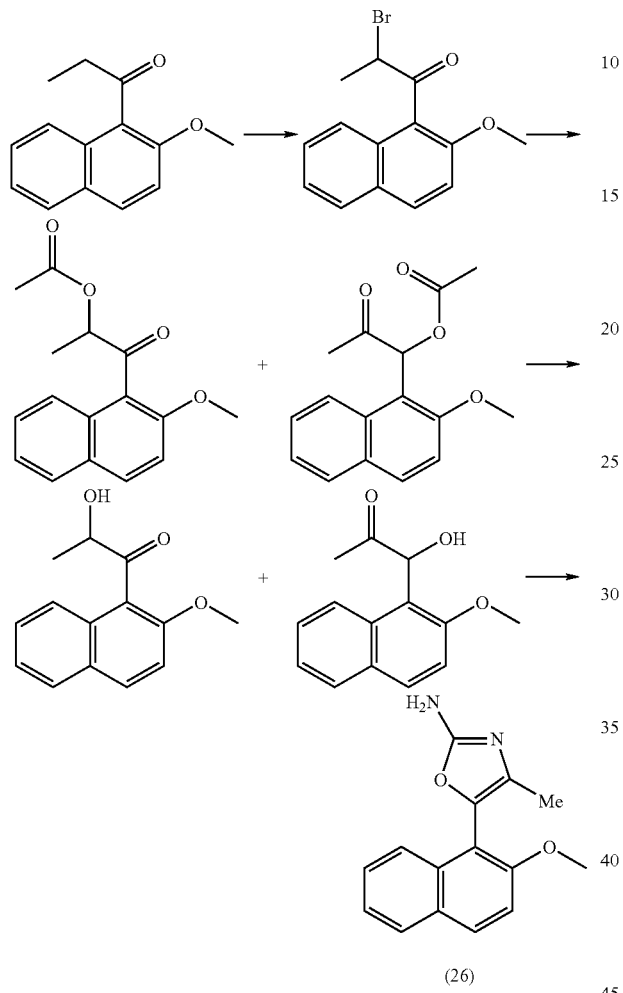

(26)

a. 2-bromo-1-(2-methoxy-naphthalen-1-yl)-propan-1-one 2-bromo-1-(2-methoxy-naphthalen-1-yl)-propan-1-one was prepared from (2-methoxy-naphthalen-1-yl)-propan-1-one according to the method of Example 16A(a) (3.0 g, 93%) as a green solid, $^1$H NMR (CDCl$_3$): 1.9 (3H, d, J=6.8 Hz), 3.9 (3H, s), 5.25 (1H, q, J=6.8 Hz), 7.25 (1H, m), 7.35 (1H, m), 7.5 (1H, m), 7.75 (2H, m), 7.9 (1H, d, J=9.2 Hz).

b. Acetic acid 1-(2-methoxy-naphthalen-1-yl)-2-oxo-propyl ester and acetic acid 2-(2-methoxy-naphthalen-1-yl)-1-methyl-2-oxo-ethyl ester (3:1 mixture)

Acetic acid 1-(2-methoxy-naphthalen-1-yl)-2-oxo-propyl ester and acetic acid 2-(2-methoxy-naphthalen-1-yl)-1-methyl-2-oxo-ethyl ester (3:1 mixture) (1.95 g, 70%) were prepared from 2-bromo-1-(2-methoxy-naphthalen-1-yl)-propan-1-one according to the method of Example 16A(b) as a dark brown gum, $^1$H NMR (CDCl$_3$): 1.45 (3H, d, J=7.2 Hz), 2.0 (3H, s), 2.05 (3H, s), 2.15 (3H, s), 3.95 (3H, s), 4.0 (3H, s), 5.25 (1H, s), 5.9 (1H, q, J=7.2 Hz), 7.2-8.0 (12H, m).

c. 2-hydroxy-1-(2-methoxy-naphthalen-1-yl)-propan-1-one and 1-hydroxy-1-(2-methoxy-naphthalen-1-yl)-propan-2-one (4.5:1 Mixture)

2-hydroxy-1-(2-methoxy-naphthalen-1-yl)-propan-1-one and 1-hydroxy-1-(2-methoxy-naphthalen-1-yl)-propan-2-one (4.5:1 mixture) (580 mg, 59%) were prepared from acetic acid 1-(2-methoxy-naphthalen-1-yl)-2-oxo-propyl ester and acetic acid 2-(2-methoxy-naphthalen-1-yl)-1-methyl-2-oxo-ethyl ester (3:1 mixture) according to the method in Example 16A(c) as an orange solid, $^1$H NMR (CDCl$_3$): 1.3 (3H, d, J=7.2 Hz), 2.0 (3H, s), 3.75 (1H, d, J=5.0 Hz), 3.9 (3H, s), 3.95 (3H, s), 4.2 (1H, d, J=3.5 Hz), 5.0 (1H, m), 5.9 (1H, d, J=3.5 Hz), 7.25-7.30 (2H, m), 7.35-7.40 (2H, m), 7.45-7.50 (2H, m), 7.6 (1H, d, J=7.7 Hz), 7.75 (2H, m), 7.85 (1H, d, J=9.0 Hz), 7.90-7.95 (2H, m).

d. 5-(2-methoxy-naphthalen-1-yl)-4-methyl-oxazol-2-ylamine 5-(2-methoxy-naphthalen-1-yl)-4-methyl-oxazol-2-ylamine (26)(35 mg, 5%) was prepared from 1-hydroxy-1-(2-methoxy-naphthalen-1-yl)-propan-2-one and 2-hydroxy-1-(2-methoxy-naphthalen-1-yl)-propan-1-one (4.5:1 mixture) according to the method in Example 16A(d) as a white solid, $^1$H NMR (DMSO-D6): 1.9 (3H, s), 3.9 (3H, s), 7.4 (1H, ddd, J=8.1, 6.8, 1.3 Hz), 7.5 (1H, ddd, J=8.5, 6.8, 1.3 Hz), 7.55 (1H, d, J=9.1 Hz), 7.7 (1H, d, J=8.5 Hz), 7.9 (1H, d, J=8.1 Hz), 8.1 (1H, d, J=9.1 Hz), 9.1 (2H, br s). Mass Spectrum (m/z): 255 (M+H)$^+$.

EXAMPLE 17

Synthesis of 4-chloromethyl-5-naphthalen-1-yl-oxazol-2-ylamine (27)

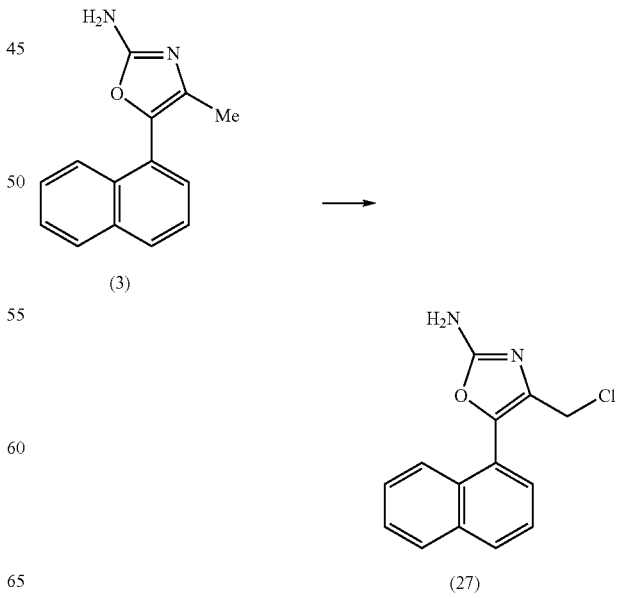

A solution of 4-methyl-5-naphthalen-1-yl-oxazol-2-ylamine (3, 800 mg), N-chlorosuccinimide (480 mg) and dichloromethane (30 mL) were irradiated with a 150W (tungsten/halogen) lamp at reflux for 8 hours. After cooling to room temperature, the solution was diluted with dichloromethane (50 mL) and washed with a saturated solution of sodium hydrogen carbonate (50 mL), water (50 mL) and brine (50 mL). The solvent was removed under reduced pressure and the resultant residue was purified by column chromatography affording 4-chloromethyl-5-naphthalen-1-yl-oxazol-2-ylamine (27) (411 mg, 45%) as an orange foam, $^1$H NMR (DMSO-D6): 4.45 (2H, s), 6.95 (2H, br s), 7.5-7.6 (4H, m), 7.95-8.00 (3H, m).

EXAMPLE 18

Synthesis of acetic acid 2-amino-5-naphthalen-1-yl-oxazol-4-ylmethyl ester (28)

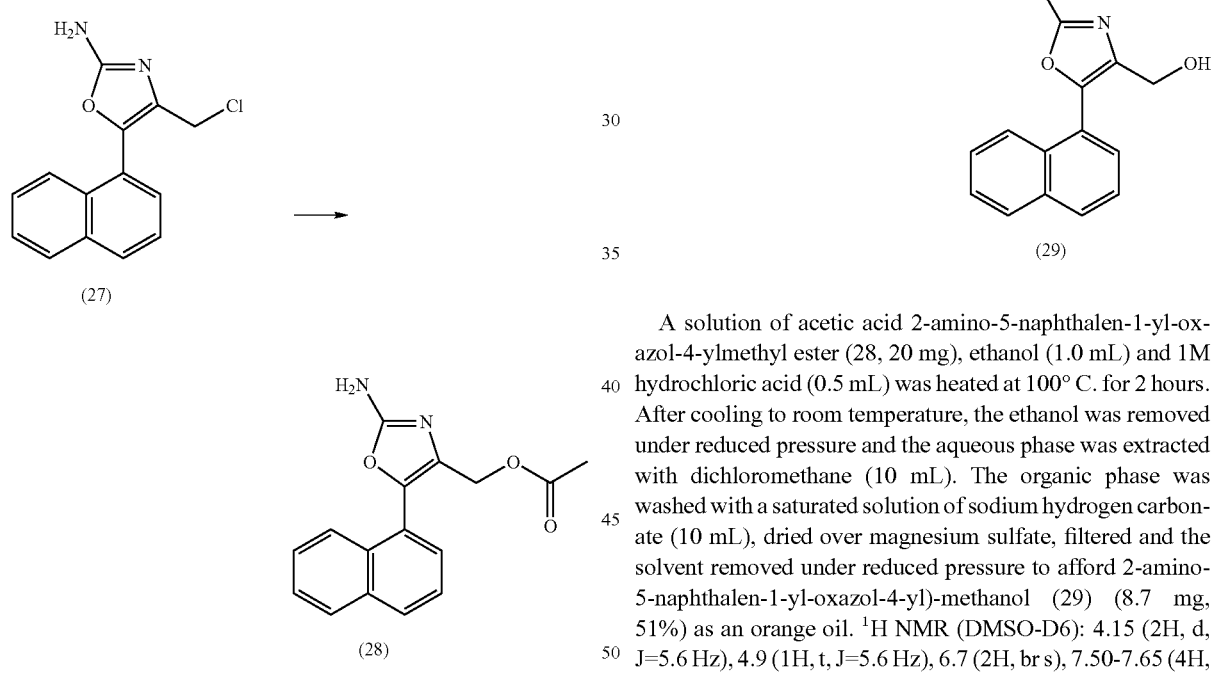

A mixture of 4-chloromethyl-5-naphthalen-1-yl-oxazol-2-ylamine (27, 80 mg), sodium acetate (32 mg) and N,N-dimethylformamide (1.75 mL) was heated at 100° C. for 2 hours.

After cooling to room temperature the N,N-dimethylformamide was removed under reduced pressure and the resulting residue was partitioned between dichloromethane (10 mL) and water (10 mL). The organic phase was washed with water (10 mL), brine (10 mL), dried over magnesium sulfate, filtered and the solvent removed under reduced pressure to afford acetic acid 2-amino-5-naphthalen-1-yl-oxazol-4-ylmethyl ester (28) (35 mg, 40%) as a yellow oil. $^1$H NMR (DMSO-D6): 1.95 (3H, s), 4.75 (2H, s), 6.85 (2H, br s), 7.45-7.55 (4H, m), 7.95-8.00 (3H, m). Mass Spectrum (m/z): 283 (M+H)$^+$.

EXAMPLE 19

Synthesis of 2-amino-5-naphthalen-1-yl-oxazol-4-yl)-methanol (29)

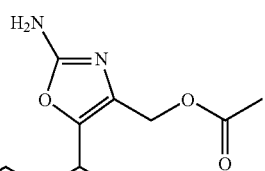

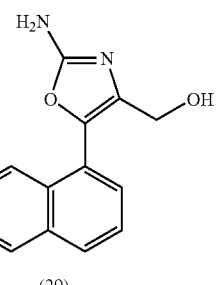

A solution of acetic acid 2-amino-5-naphthalen-1-yl-oxazol-4-ylmethyl ester (28, 20 mg), ethanol (1.0 mL) and 1M hydrochloric acid (0.5 mL) was heated at 100° C. for 2 hours. After cooling to room temperature, the ethanol was removed under reduced pressure and the aqueous phase was extracted with dichloromethane (10 mL). The organic phase was washed with a saturated solution of sodium hydrogen carbonate (10 mL), dried over magnesium sulfate, filtered and the solvent removed under reduced pressure to afford 2-amino-5-naphthalen-1-yl-oxazol-4-yl)-methanol (29) (8.7 mg, 51%) as an orange oil. $^1$H NMR (DMSO-D6): 4.15 (2H, d, J=5.6 Hz), 4.9 (1H, t, J=5.6 Hz), 6.7 (2H, br s), 7.50-7.65 (4H, m), 7.9-8.0 (3H, m). Mass Spectrum (m/z): 241 (M+H)$^+$.

EXAMPLE 20

Synthesis of 5-Methyl-4-naphthalen-1-yl-oxazol-2-ylamine (30)

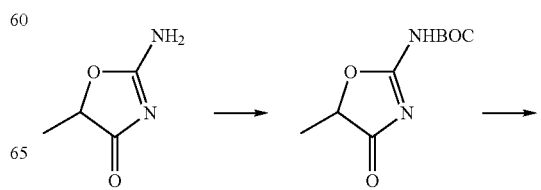

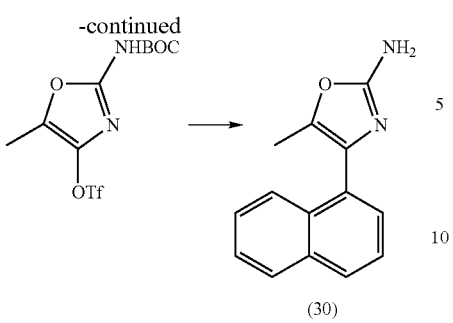

a. (5-Methyl-4-oxo-4,5-dihydro-oxazol-2-yl)-carbamic acid tert-butyl ester

A solution of 2-amino-5-methyl-oxazol-4-one (7.9 g), 4-(dimethylamino)pyridine (20 mg), di-tert-butyldicarbonate (16.6 g), triethylamine (21 mL) and N,N-dimethylformamide (80 mL) was stirred at room temperature for 3 days. The solvent was removed under reduced pressure and the resulting yellow solid was washed with diethyl ether to afford (5-methyl-4-oxo-4,5-dihydro-oxazol-2-yl)-carbamic acid tert-butyl ester (8.3 g, 68%) as a white solid; $^1$H NMR (DMSO-D6): 1.35 (3H, d, J=7.0 Hz), 1.4 (9H, br s), 3.0 (1H, s), 4.8 (1H, q, J=7.0 Hz); Mass Spectrum (m/z): 215 (M+H)$^+$.

b. Trifluoro-methanesulfonic acid 2-tert-butoxycarbonylamino-5-methyl-oxazol-4-yl ester A solution of (5-methyl-4-oxo-4,5-dihydro-oxazol-2-yl)-carbamic acid tert-butyl ester (4.0 g), trifluoromethanesulfonic anhydride (4.7 mL), 2,6-lutidine (4.4 mL) and dichloromethane (50 mL) was stirred at room temperature for 3 days. The solvent was removed under reduced pressure and the resulting brown solid was washed with ethanol to afford trifluoro-methanesulfonic acid 2-tert-butoxycarbonylamino-5-methyl-oxazol-4-yl ester (2.0 g, 31%) as a white solid; $^1$H NMR (CDCl$_3$): 1.5 (9H, s), 2.3 (3H, s), 7.55 (1H, br s); Mass Spectrum (m/z): 347 (M+H)$^+$.

c. Syntheis of 5-Methyl-4-naphthalen-1-yl-oxazol-2-ylamine (30)

A mixture of trifluoro-methanesulfonic acid 2-tert-butoxycarbonylamino-5-methyl-oxazol-4-yl ester (100 mg), 1-naphthaleneboronic acid (61 mg) palladium (0) tetrakis (triphenylphosphine) (17 mg), potassium acetate (85 mg) and 1,4-dioxane (5 mL) was heated at 180° C. for 24 hours. The solvent was removed under reduced pressure and to the resulting yellow oil was added dichloromethane (18 mL) and trifluoroacetic acid (2 mL). The mixture was stirred at room temperature for 1 hour and then the solvent was removed under reduced pressure, the resulting oil was diluted with ethyl acetate and washed with a saturated solution of sodium hydrogen carbonate, brine, dried over magnesium sulfate, filtered and the solvent removed under reduced pressure to afford a brown oil. Purification by column chromatography afforded 5-methyl-4-naphthalen-1-yl-oxazol-2-ylamine (30) (9 mg, 14%) as a white solid. $^1$H NMR (DMSO-D6): 2.15 (3H, s), 6.5 (2H, br s), 7.4-7.5 (4H, m), 7.85-7.90 (2H, m), 8.2 (1H, m). Mass Spectrum (m/z): 225 (M+H)$^+$.

EXAMPLE 21

Synthesis of 2-amino-5-(4'-fluoronaphth-1-yl)-4-isopropyloxazole (31)

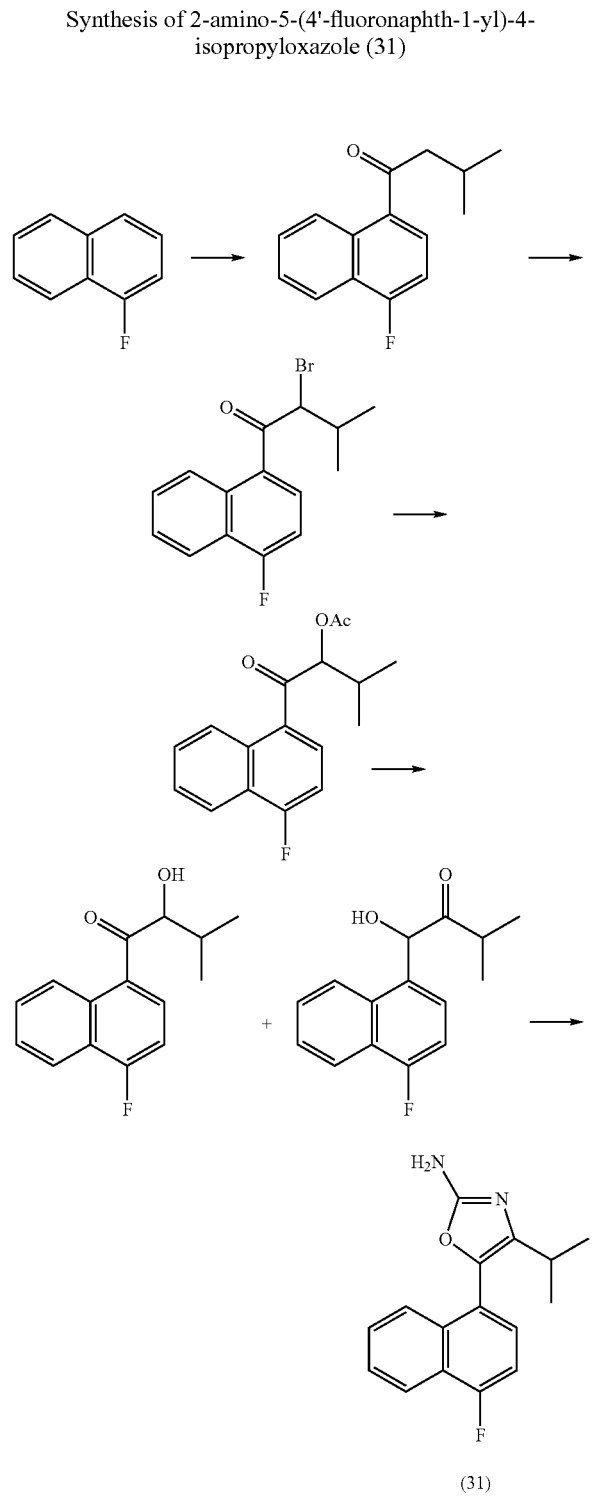

a. 1-(4'-fluoronaphth-1-yl)-3-methylbutan-1-one

To an ice/salt cooled solution of 1-fluoronaphthalene (5.1 g) in anhydrous dichloromethane (20 ml) was added aluminium chloride (5.6 g). After 5 minutes, a solution of isovaleryl chloride (4.2 g) in anhydrous dichloromethane (5 ml) was added dropwise over 20 minutes. The mixture was allowed to warm to room temperature overnight, then added cautiously to a vigorously stirred mixture of ice water and dichloromethane. The organic layer was separated, clarified with methanol, washed with brine, dried with sodium sulphate, filtered and evaporated in vacuo. The title compound (7 g) was obtained following silica gel column chromatography of the residue in 20-40% dichloromethane in petroleum ether.

$^1$H NMR (CDCl$_3$, δ): 0.95 (6H, d); 2.3 (1H, septet); 2.9 (2H, d); 5.8 (1H, d); 7.05 (1H, dd); 7.6 (2H, m); 7.8 (1H, m); 8.1 (1H, d); 8.65 (1H, d).

b. 2-acetoxy-1-(4'-fluoronaphth-1-yl)-3-methylbutan-1-one

To a solution of 3-methyl-1-(4'-fluoronaphth-1-yl)butan-1-one (7 g) in anhydrous tetrahydrofuran (80 ml) was added phenyltrimethylammonium tribromide (11.5 g). The resulting mixture was stirred overnight at ambient temperature then partitioned between petroleum ether and water. The organic layer was separated, washed with water, brine, dried with sodium sulphate, filtered and evaporated in vacuo to yield crude 2-bromo-1-(4'-fluoronaphth-1-yl)-3-methylbutan-1-one. Sodium acetate (2.75 g) and anhydrous dimethylformamide (30 ml) were added and the resulting mixture was stirred at 80° C. for 5 hours. After cooling, the mixture was partitioned between ethyl acetate and water. The aqueous layer was back-extracted once with ethyl acetate. The combined organic layers were washed with water, brine, dried with sodium sulphate, filtered and evaporated in vacuo. The title compound (4.8 g) was obtained following silica gel column chromatography of the residue in 30-100% dichloromethane in petroleum ether.

$^1$H NMR (CDCl$_3$, δ): 0.95 (6H, t); 2.2 (3H, s); 2.2 (1H, m); 5.7 (1H, d); 7.2 (1H, dd); 7.65 (2H, m); 7.95-8.2 (2H, m); 8.5 (1H, m).

c. 2-amino-5-(4'-fluoronaphth-1-yl)-4-isopropyloxazole (31)

A mixture of 2-acetoxy-3-methyl-1-(4'-fluoronaphth-1-yl)butan-1-one (4.8 g), IMS (100 ml) and hydrochloric acid (1M; 70 ml) were boiled under reflux for 4 hours. The mixture was cooled, evaporated in vacuo and partitioned between dichloromethane and brine. The organic layer was separated, dried with sodium sulphate, filtered and evaporated in vacuo. The residue was purified by silica gel column chromatography in 66-100% dichloromethane in petroleum ether to afford a mixture of 2-hydroxy-3-methyl-1-(4'-fluoronaphth-1-yl)butan-1-one and 1-hydroxy-3-methyl-1-(4'-fluoronaphth-1-yl)butan-2-one (3.2 g). Cyanamide (0.65 g) and anhydrous ethanol (10 ml) were added and the resulting mixture was boiled under reflux for 48 hours. After cooling the volatiles were removed in vacuo and the residue heated at 110° C. for a further 48 hours. The mixture was cooled, triturated with chloroform (100 ml) and filtered. The filtrate was washed with water, dried with sodium sulphate, filtered and evaporated in vacuo. The title compound (0.25 g; m.p. 141° C., softens from 125° C.) was obtained following silica gel column chromatography of the residue in 50% ethyl acetate in petroleum ether.

$^1$H NMR (CDCl$_3$, δ): 1.2 (6H, d); 2.8 (1H, septet); 4.9 (2H, broad s); 7.15 (2H, dd); 7.4 (2H, dd); 7.6 (2H, m); 7.95 (1H, m); 8.15 (1H, m). Mass spectrum (m/z): 271.1 (M+H)$^+$ Microanalysis: C expected 71.10 found 71.04; H expected 5.59 found 5.75; N expected 10.36 found 10.31.

Human Cloned 5-HT$_{2B}$ Receptor Binding Assay

The binding affinity of the compounds for human cloned 5-HT$_{2B}$ receptors was determined using the following assay.

CHO-K1 cells expressing cloned 5-HT$_{2B}$ receptor were maintained in Ultra-CHO medium containing 400 µg/ml of G418, 100 U/ml penicillin, 100 µg/ml streptomycin, 2.5 µg/ml fungizone and 1% foetal bovine serum, in 95/5% O$_2$/CO$_2$ at 37° C. The cells were harvested using 0.25% trypsin and were centrifuged at 800 rpm for 8 minutes. The cells were homogenised in 50 mM HEPES buffer containing 1 mM disodium EDTA and 1 mM PMSF at pH 7.4, using a Dounce homogeniser (20 strokes). The homogenate was centrifuged at 2280 rpm (1000 g) and 4° C. for 10 minutes, after which the supernatant was removed by decanting. The pellet was re-homogenised as above, and the resulting supernatant removed and combined with that already obtained. The supernatant solution was then centrifuged at 18300 rpm (40000 g) for 10 minutes at 4° C. using a Sorvall centrifuge. The supernatant was removed, and the pellet was re-suspended in 50 mM buffer at pH 7.4 using a Ultra-turrax T25 Polytron, before centrifugation again at 40000 g as above. This wash procedure was repeated, after which the membrane preparation was stored at a concentration of 1 mg/ml at −80° C. until use.

The membranes were thawed rapidly and diluted in assay buffer containing Tris-HCl (50 mM, pH 7.4), ascorbic acid (0.1%) and calcium chloride (4 mM). The membranes were homogenised to resuspend them, prior to adding 10 or 15 µg of membranes to assay wells containing [$^3$H]LSD (1 nM), assay buffer (50 mM Tris, 4 mM calcium chloride and 0.1% ascorbic acid) containing pargyline (10 µM), and the test compounds (1×10$^{-10}$ to 1×10$^{-4}$M). Non specific binding was determined in the presence of 100 µM 5-HT. After 30 minutes incubation at 37° C., the assay mixture was filtered through a combination of GF-C and GF-B filters, pre-soaked in 1% polyethyleneimine, using a Brandel cell harvester, and were washed three times using 50 mM Tris-HCl. Radioactivity retained on the filters was determined by liquid scintillation counting. For each test compound, the concentration that inhibited binding of [3H]LSD by 50% was determined using curve fitting software (Prism). Kd values (concentration of LSD required to occupy 50% of the receptor binding sites at equilibrium) determined from saturation binding studies were then used to calculate inhibition dissociation constants (Ki) using the following equation:

$$Ki = \frac{IC_{50}}{1 + \left(\frac{\text{Radioligand concentration}}{\text{Radioligand } Kd}\right)}$$

The results are shown in table 1 below as pKi values. This approach follows that set out in Kenakin, T.P. Pharmacologic analysis of drug-receptor interaction. Raven Press, New York, 2$^{nd}$ Edition.

Human 5-HT2A and 5-HT$_{2C}$ Receptor Binding Assays

The binding affinity of ligands for human 5-HT$_{2A}$ and 5-HT$_{2C}$ receptors was determined using the following assay. These results were then used to determine the selectivity of the test compounds for 5-HT$_{2B}$ receptors, over 5-HT$_{2A}$ and 5-HT$_{2C}$ receptors.

Membrane preparations from CHO-K1 cells expressing the cloned human 5-HT$_{2A}$ receptor were obtained (Euroscreen). The membranes were thawed rapidly and diluted in assay buffer containing Tris-HCl (50 mM, pH 7.7). The membranes were resuspended by homogenisation, prior to adding 15 µg of membranes to assay wells containing [3H] ketanserin (1 nM), assay buffer (50 mM Tris at pH 7.4) containing pargyline (10 µM), and test compounds (1×10$^{-10}$ to 1×10$^{-4}$M). Non specific binding was determined in the presence of 100 µM mianserin. After 15 minutes incubation at 37° C., the assay mixture was filtered through a combination of GF-C and GF-B filters, pre-soaked in 0.05% Brij, using a Brandel cell harvester, and were washed three times using ice cold Tris-HCl buffer (50 mM). Radioactivity retained on the filters was determined by liquid scintillation counting. For each test compound, the concentration that inhibited binding of [$^3$H]ketanserin by 50% was determined using curve fitting software (Prism). Kd values (concentration of ketanserin required to occupy 50% of the receptor binding sites at equlibrium) determined from saturation binding studies were then used to calculate inhibition dissociation constants (Ki) using the following equation:

$$Ki = \frac{IC_{50}}{1 + \left(\frac{\text{Radioligand concentration}}{\text{Radioligand } Kd}\right)}$$

Membrane preparations from CHO-K1 cells expressing the cloned human 5-HT$_{2C}$ receptor were obtained (Euroscreen). The membranes were thawed rapidly and diluted in assay buffer containing Tris-HCl (50 mM, pH 7.7), ascorbic acid (0.1%) and pargyline (10 µM). The membranes were resuspended by homogenisation, prior to adding 6 µg of membranes to assay wells containing [$^3$H] mesulergine (1 nM), assay buffer (50 mM Tris at pH 7.7 and 0.1% ascorbic acid) containing pargyline (10 µM), and test compounds ($1\times10^{-10}$ to $1\times10^{-4}$M). Non specific binding was determined in the presence of 100 µM mianserin. After 30 minutes incubation at 37° C., the assay mixture was filtered through a combination of GF-C and GF-B filters, pre-soaked in 1% bovine serum albumin, using a Brandel cell harvester, and were washed three times using ice cold Tris-HCl buffer (50 mM). Radioactivity retained on the filters was determined by liquid scintillation counting. For each test compound, the concentration that inhibited binding of [3H]mesulergine by 50% was determined using curve fitting software (Prism). Kd values (concentration of mesulergine required to occupy 50% of the receptor binding sites at equlibrium) determined from saturation binding studies were then used to calculate inhibition dissociation constants (Ki) using the following equation:

$$Ki = \frac{IC_{50}}{1 + \left(\frac{\text{Radioligand concentration}}{\text{Radioligand } Kd}\right)}$$

The results are shown in table 1 below as pKi values.

TABLE 1

| Compound | 5-HT$_{2B}$ | 5-HT$_{2A}$ | 5-HT$_{2C}$ |
|---|---|---|---|
| 1 | >7 | <5 | <6 |
| 2 | >6 | <5 | <6 |
| 3 | >8 | <5 | <5 |
| 4 | >7 | <6 | <6 |
| 5 | >7 | <6 | <6 |
| 6 | >8 | <6 | <6 |
| 7 | >8 | <7 | <6 |
| 8 | >6 | <5 | <5 |
| 9 | >6 | <5 | <6 |
| 10 | >8 | <6 | <6 |
| 11 | >7 | <5 | <5 |
| 12 | >6 | | |
| 13 | >6 | <5 | <6 |
| 14 | >6 | <5 | <5 |
| 15 | >6 | <6 | <6 |
| 16 | >6 | <5 | <5 |
| 17 | >8 | <6 | <7 |
| 18 | >6 | <5 | <5 |
| 19 | >5 | <5 | <6 |
| 20 | >5 | <5 | <5 |
| 21 | >5 | <5 | <6 |
| 22 | >7 | <6 | |
| 23 | >6 | | <5 |
| 24 | >5 | <5 | <5 |
| 25 | >7 | <6 | <6 |
| 26 | >8 | <6 | |
| 28 | >7 | <5 | |
| 29 | >7 | | <6 |
| 30 | >7 | <5 | |
| 31 | >8 | <6 | <6 |

Human 5-HT$_{2B}$ Receptor Tissue Based Functional Assay

An in vitro functional assay, using human colon smooth muscle, was carried out to determine the affinity of the test compounds at the 5-HT$_{2B}$ receptor in human tissues.

Sections of human colon were cut open along their longitudinal axis. The sections were pinned out flat and the mucosa carefully removed using sharp dissecting scissors. Once the mucosa was removed, the section was turned over to reveal the three *taenia coli* (*taenia mesencolica*, *taenia omentalis* and *taenia libera*) and the muscle bands that lie between them. Longitudinal muscle strips (2 mm wide by 20 mm long) were then cut from the tissue between the *taenia coli* and suspended between stainless steel hooks in organ chambers containing oxygenated (95% O$_2$/5% CO$_2$) Krebs solution at 37° C. The composition of the Krebs solution was as follows: NaCl (118.2 mM), KCl (4.69 mM), MgSO$_4$.7H$_2$O (1.18 mM), KH$_2$PO$_4$ (1.19 mM), glucose (11.1 mM), NaHCO$_3$ (25.0 mM), CaCl$_2$.6H$_2$O (2.5 mM).

Tissues were placed under a load equivalent to 10 mN and left to equilibrate for a period of at least 60 minutes. Responses were recorded using isometric transducers coupled to an Apple Macintosh computer via a MacLab interface. After 60 minutes, the longitudinal muscle sections of the human colon were stimulated electrically (sub-maximal voltage and frequency with 60s between successive stimulations) using parallel platinum wire electrodes and a Multistim D330 pulse stimulator. Upon electrical stimulation, the strips of human colon longitudinal smooth muscle responded with a rapid contraction. Once the response to electrical stimulation had stabilised (stimulated responses differed by no more than 10%), the strips were exposed to increasing concentrations of 5-HT ($1\times10^{-9}$ to $1\times10^{-5}$M), in the absence or presence of test compounds ($1\times10^{-7}$ to $1\times10^{-5}$M, incubated for 30 minutes). To determine the affinity of the compounds, the concentration of 5-HT required to produce half-maximal effects (EC$_{50}$) was calculated in the absence and presence of test compound. The antagonist affinity was calculated by dividing the EC$_{50}$ for 5-HT in the presence of antagonist by the EC$_{50}$ for 5-HT in the absence of antagonist to yield a concentration ratio (CR).

The results are shown in table 2 below as a pKB value, which is calculated as follows:

$pKB=\log(CR-1)-\log(\text{antagonist concentration}).$

This approach follows that set out in Kenakin, T. P. Pharmacologic analysis of drug-receptor interaction. Raven Press, New York, 2nd Edition.

TABLE 2

| Compound | Colon |
|----------|-------|
| 1  | >7 |
| 6  | >7 |
| 7  | >8 |
| 17 | >8 |
| 31 | >7 |

Human Cloned 5-$HT_{2B}$ Cell-based Functional Assay

The following describes an in vitro functional assay using human cloned 5-$HT_{2B}$ receptors to determine the ability of compounds to block the receptor.

CHO.K1 cells expressing cloned 5-HT2B receptor were maintained In Ultra-CHO medium containing 400 μg/ml of G418, 100 U/ml penicillin, 100 μg/ml streptomycin, 2.5 μg/ml fungizone, in 95/5% $O_2/CO_2$ at 37° C. Ultra-CHO medium additionally supplemented with 1% foetal bovine serum was used when seeding the cells and removed after 5 hours. Cells were plated in Costar 96 well white, clear-bottomed plate at a density of 50,000 cells per well and incubated for at least 24 hours in 95/5% $O_2/CO_2$ at 37° C. before running the assay.

Media was removed from the wells and 200 μl of 4 μM Fluo-4 AM added, this was incubated in a Wallace Victor 2V workstation at 37° C. for 30 minutes. The Fluo-4 AM was then removed from the wells, which were then washed twice with 200 μl of buffer (HBSS without calcium/magnesium/phenol red, 20 mM HEPES, 1 mM $Ca^{2+}$, 1 mM $Mg^{2+}$, 2.5 mM probenecid, pH to 7.4), 180 μl of buffer or test compound was added to the well and incubated for 30 minutes. The Victor 2V injectors were used to inject 20 μl of 5-HT after obtaining 10 0.1-second baseline readings at 535 nm, followed by 150 readings.

All test compounds were aliquoted in 100% DMSO at 10 mM and diluted to 1 mM in 50% DMSO, subsequent dilutions were made using buffer. Buffer was also used to dilute the 5-HT. Data were analysed using Microsoft Excel and GraphPad Prism, with the latter used to produce sigmoidal dose-response curves for each compound. The compound concentration that inhibited the 5-HT response by 50% was taken ($IC_{50}$-M), and the results are shown in Table 3, as $pIC_{50}$, being the negative log (to the base 10) of the measured $IC_{50}$ values.

TABLE 3

| Compound | $pIC_{50}$ |
|----------|------------|
| 1  | >7 |
| 2  | >5 |
| 3  | >7 |
| 6  | >7 |
| 7  | >8 |
| 16 | >5 |
| 17 | >8 |
| 25 | >6 |
| 31 | >8 |

The invention claimed is:

1. A pharmaceutical composition comprising a compound of formula I:

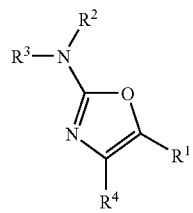

(I)

or a pharmaceutically acceptable salt thereof, together with a pharmaceutically acceptable carrier or diluent, wherein $R^4$ is selected from the group consisting of H, and optionally substituted $C_{1-6}$ alkyl, $C_{3-7}$ cycloalkyl, $C_{3-7}$ cycloalkyl-$C_{1-4}$ alkyl, and phenyl-$C_{1-4}$ alkyl;

$R^1$ is an optionally substituted $C_{9-14}$ aryl group comprising at least two fused rings;

$R^2$ and $R^3$ are either:
(i) independently selected from H, R, R', $SO_2R$, C(=O)R, $(CH_2)_nNR^5R^6$, where n is from 1 to 4 and $R^5$ and $R^6$ are independently selected from H and R, where R is optionally substituted $C_{1-4}$ alkyl, and R' is optionally substituted phenyl-$C_{1-4}$ alkyl, or
(ii) together with the nitrogen atom to which they are attached, form an optionally substituted $C_{5-7}$ heterocyclic group.

2. A pharmaceutical composition according to claim 1, wherein $R^4$ is selected from H and optionally substituted $C_{1-6}$ alkyl and $C_{3-7}$ cycloalkyl.

3. A pharmaceutical composition according to claim 1, wherein $R^2$ and $R^3$ independently selected from H, R and R'.

4. A pharmaceutical composition according to claim 1, wherein $R^1$ is an optionally substituted $C_{9-14}$ carboaryl group.

5. A pharmaceutical composition according to claim 1, wherein the optional substituent groups for the $C_{9-14}$ aryl group are selected from halo, hydroxy, $C_{1-4}$ alkoxy, cyano, amino, amido and $C_{1-4}$ alkyl.

6. A pharmaceutical composition according to claim 1, wherein the $C_{9-14}$ aryl group bears no oxo substituents.

7. A pharmaceutical composition according to claim 1, wherein the optional substituents for $R^1$, $R^2$, $R^3$ and $R^4$ are independently selected from halo, hydroxy, alkoxy, amino, and amido.

8. A compound of formula I:

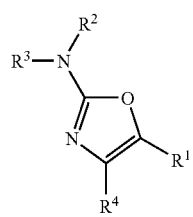

(I)

or a salt, solvate and chemically protected form thereof, wherein $R^4$ is selected from the group consisting of H, and optionally substituted $C_{1-6}$ alkyl, $C_{3-7}$ cycloalkyl, $C_{3-7}$ cycloalkyl-$C_{1-4}$ alkyl, and phenyl-$C_{1-4}$ alkyl;

R¹ is an optionally substituted $C_{9-14}$ aryl group comprising at least two fused rings;

R² and R³ are either:
(i) independently selected from H, R, R', $SO_2R$, C(=O)R, $(CH_2)_nNR^5R^6$, where n is from 1 to 4 and R⁵ and R⁶ are independently selected from H and R, where R is optionally substituted $C_{1-4}$ alkyl, and R' is optionally substituted phenyl-$C_{1-4}$ alkyl, or
(ii) together with the nitrogen atom to which they are attached, form an optionally substituted $C_{5-7}$ heterocyclic group.

9. A compound according to claim 8, wherein R⁴ is selected from H and optionally substituted $C_{1-6}$ alkyl and $C_{3-7}$ cycloalkyl.

10. A compound according to claim 8, wherein R² and R³ independently selected from H, R and R'.

11. A compound according to claim 8, wherein R¹ is an optionally substituted $C_{9-14}$ carboaryl group.

12. A compound according to claim 8, wherein the optional substituent groups for the $C_{9-14}$ aryl group are selected from halo, hydroxy, $C_{1-4}$ alkoxy, cyano, amino, amido and $C_{1-4}$ alkyl.

13. A compound according to claim 8, wherein the $C_{9-14}$ aryl group bears no oxo substituents.

14. A compound according to claim 8, wherein the optional substituents for R¹, R², R³ and R⁴ are independently selected from halo, hydroxy, alkoxy, amino, and amido.

15. A pharmaceutical composition comprising 5-(2-methoxy-naphthalen-1-yl)-oxazol-2-ylamine, or a pharmaceutically acceptable salt thereof, together with a pharmaceutically acceptable carrier or diluent.

16. The compound 5-(2-methoxy-naphthalen-1-yl)-oxazol-2-ylamine, or a pharmaceutically acceptable salt thereof.

* * * * *